(12) United States Patent
Baricevic et al.

(10) Patent No.: US 11,363,963 B2
(45) Date of Patent: Jun. 21, 2022

(54) METHOD AND DEVICE FOR DETERMINING THE HYDRATION, FITNESS AND NUTRITION STATUS OF A HUMAN BODY

(71) Applicants: Borut Baricevic, Koper Capodistria (SI); James R. Matthie, La Jolla, CA (US)

(72) Inventors: Borut Baricevic, Koper Capodistria (SI); James R. Matthie, La Jolla, CA (US)

(*) Notice: Subject to any disclaimer, the term of this patent is extended or adjusted under 35 U.S.C. 154(b) by 230 days.

(21) Appl. No.: 16/500,639

(22) PCT Filed: Apr. 4, 2018

(86) PCT No.: PCT/IB2018/000319
§ 371 (c)(1),
(2) Date: Oct. 3, 2019

(87) PCT Pub. No.: WO2018/185550
PCT Pub. Date: Oct. 11, 2018

(65) Prior Publication Data
US 2020/0113479 A1    Apr. 16, 2020

Related U.S. Application Data

(60) Provisional application No. 62/481,378, filed on Apr. 4, 2017.

(51) Int. Cl.
*A61B 5/053*    (2021.01)
*A61B 5/00*     (2006.01)
*A61B 5/0537*   (2021.01)

(52) U.S. Cl.
CPC .......... *A61B 5/0537* (2013.01); *A61B 5/4872* (2013.01); *A61B 5/4875* (2013.01); *A61B 5/6824* (2013.01); *A61B 5/6829* (2013.01)

(58) Field of Classification Search
CPC ................ A61B 5/0537; A61B 5/4872; A61B 5/4875; A61B 5/4878; A61B 5/4881; A61B 5/4869; A61B 5/6824; A61B 5/6829
See application file for complete search history.

(56) References Cited

U.S. PATENT DOCUMENTS 5,449,000 A  *  9/1995  Libke ................... A61B 5/0537
                                                              600/547
7,072,710 B2    7/2006  Chamney
                        (Continued)

FOREIGN PATENT DOCUMENTS

DE    60128582 T2  *  1/2008  ........... A61B 5/0535
JP    2016150098 A  *  8/2016  ............... A61B 5/05

OTHER PUBLICATIONS

P Deurenberg, Limitations of the bioelectrical impedance method for the assessment of body fat in severe obesity, The American Journal of Clinical Nutrition, vol. 64, Issue 3, Sep. 1996, pp. 449S-452S (Year: 1996).*

(Continued)

*Primary Examiner* — Sean P Dougherty
*Assistant Examiner* — Jonathan E. Cooper
(74) *Attorney, Agent, or Firm* — Locke Lord LLP; Daniel J. Fiorello

(57) ABSTRACT

A method for determining the hydration, fitness and/or nutrition status of a human body, or of segments of the human body, comprises providing values each of a mass or volume fraction of intracellular water and a mass or volume fraction of extracellular water of the human body or the segment, defining a two-dimensional parameter space, determining a reference line within the parameter space, locating a position within the parameter space which corresponds to the associated values of the mass or volume fraction of intracellular water and the mass or volume fraction of extracellular water of the human body or the segment, (Continued)

determining a distance between the position and the reference line, and deriving a mass or volume, or a mass or volume fraction, of hydration from the determined distance from the reference line for the human body or the segment.

13 Claims, 7 Drawing Sheets

(56) References Cited

U.S. PATENT DOCUMENTS

| | | | |
|---|---|---|---|
| 7,133,716 | B2 | 11/2006 | Kraemer et al. |
| 7,917,202 | B2 | 3/2011 | Chamney et al. |
| 8,340,754 | B2 | 12/2012 | Chamney et al. |
| 2004/0167423 | A1 | 8/2004 | Pillon et al. |
| 2005/0039763 | A1 | 2/2005 | Kraemer et al. |
| 2008/0071147 | A1* | 3/2008 | Chamney ............. A61B 5/0537 600/300 |
| 2013/0211278 | A1 | 8/2013 | Chamney et al. |
| 2015/0359467 | A1 | 12/2015 | Tran |
| 2016/0169861 | A1 | 6/2016 | Chamney et al. |

OTHER PUBLICATIONS

International Search Report issued in corresponding PCT patent Application No. PCT/IB2018/000319, dated Sep. 18, 2018.
Chamney et al. (2007): "A whole-body model to distinguish excess fluid from the hydration of major body tissues", Am. J. Clin. Nutr. 2007, vol. 85, p. 80-89.
Moissl, U.M., Wabel P., Chamney P.W., Bosaeus I., Levin N.W., Bosy Westphal A., Korth O., Müller M.J., Ellegård L., Malmros V., Kaitwatcharachai C., Kuhlmann M.K., Zhu F., Fuller N.J. (2006): "Body fluid volume determination via body composition spectroscopy in health and disease" in: Physiol. Meas. 27, 921-933.
Antonelou, M.; El-Kateb S.; Davies N.; Davenport A. (2016): "Changes in serum osmotic pressure following haemodialysis treatments lead to changes in bioimpedance spectroscopy estimates of lean and adipose tissue" in European Journal of Clinical Nutrition, Feb. 1, 2017. doi: 10.1038/ejcn.2016.270.
Barac-Nieto, M., Spurr, G.B., Lotero, H. and Maksud, M.G. (1978): "Body Composition in Chronic undernutrition" in The America Journal of Clinical Nutrition 31, 23-40.
Xitron Hydra ECF/ICF (Model 4200) Bioimpedance spectrum analyzer, Issue 1.01 Jun. 1997 (1997), Operating Manual Revision 1.01 Xitron Technologies Inc.: San Diego, USA.
Matthie, J.R. (2005): "Second generation mixture theory equation for estimating intracellular water using bioimpedance spectroscopy", J. Appl. Physiol. 99, 780-1 (2005).
Berstad P., Randby A., Seim Ekeland G., Ulveland H., Omland T., Almendingen K.: "Body fat and fat-free mass measured by bioelectric impedance spectroscopy and dual-energy X-ray absorptiometry in obese and non-obese adults" in the British Journal of Nutrition (Apr. 2012); 107(8):1192-200.
L.H. Ellegård, M. Åhlen, U. Körner, K. G. Lundholm, L. D. Plank and I. G. Bosaeus (2009); "Bioelectric impedance spectroscopy underestimates fat-free mass compared to dual energy X-ray absorptiometry in incurable cancer patients" in: European Journal of Clinical Nutrition (2009) 63, 794-801.
National Health and Nutrition Examination Survey (NHANES): "NHANES 1999-2006 DXA Multiple Imputation Data Files: The 1999-2006 Dual Energy X-ray Absorptiometry (DXA) Multiple Imputation Data Files and Technical Documentation" (2006): download link under https://wwwn.cdc.gov/Nchs/Nhanes/Dxa/Dxa.aspx (valid on Dec. 23, 2019), U.S. Department of Health and Human Services, Centers for Disease Control and Prevention (CDC).
Chamney P.W., Krämer M., Rode C., Kleinekofort W., Wizemann V. Kidney (2002): "A new technique for establishing dry weight in hemodialysis patients via whole body bioimpedance", Int. Jun. 2002; 61(6):2250-8.
Kraemer, M. (2006): "A new model for the determination of fluid status and body composition from bioimpedance measurements", Physiol. Meas. Sep. 2006; 27(9):901-19.
Matthie, J.R. (2008); "Bioimpedance measurements of human body composition: critical analysis and outlook", Expert Rev Med Devices Mar. 2008;5(2):239-61. doi: 10.1586/17434440.5.2.239. Review.
Noshiro M, Morimoto T, Nagao H, Matsuda H. (1993): "Electrical impedance in the lower limbs of patients with Duchenne muscular dystrophy: a preliminary study", Med. Biol. Eng. Comput. Mar. 1993; 31(2):97-102.
Maughan R.J., Meyer N.L. (2013): "Hydration during intense exercise training", Nestle Nutr. Inst. Workshop Ser. 2013; 76:25-37. doi:10.1159/000350225.
Raja M.K., Raymer G.H., Moran G.R., Marsh G., Thompson R.T. (2006): "Changes in tissue water content measured with multiple-frequency bioimpedance and metabolism measured with 31P-MRS during progressive forearm exercise", J. Appl. Physiol. (1985). Oct. 2006; 101(4):1070-5.
Montgomery L.D., Montgomery R.W., Gerth W.A., Lew S.Q., Klein M.D., Stewart J.M., Medow M.S., Velasquez M.T. (2016): "Bioimpedance monitoring of cellular hydration during hemodialysis therapy", Hemodial Int. Nov. 8, 2016. doi 10.1111/hdi.12511.
Lukaski H.C., Johnson P.E., Bolonchuk W.W., Lykken G.I. (1985): "Assessment of fat-free mass using bioelectrical impedance measurements of the human body", Am. J. Clin. Nutr. Apr. 1985; 41(4):810-7.
Extended European search report issued in corresponding EP application No. 18781774.7, dated Sep. 23, 2020.
Mohannad W Kafri et al: "The diagnostic accuracy of multi-frequency bioelectrical impedance analysis in diagnosing dehydration after stroke",Medical Science Monitor, vol. 19, Jan. 1, 2013 (Jan. 1, 2013), pp. 548-570, XP055727009.
Nwosu et al. "The Association of Hydration Status with Physical Signs, Symptoms and Survival in Advance Cancer: The Use of Bioelectrical Impedance Vector Analysis (BIVA) Technology to Evaluate Fluid Volume in Palliative Care: An Observational Study." In: PLoS One. 2016, Sep. 27, 2016 [online] [retrieved on Aug. 28, 2018 (Aug. 28, 2018)] Retrieved from the Internet <URL: https://www.ncbi.nlm.nih.gov/pubmed/27673684, entire document, especially Abstract; Figure 1; pp. 2-5.
International Search Report and Written Opinion issued in corresponding PCT patent Application No. PCT/IB2018/000319, dated Sep. 18, 2018.

* cited by examiner

METHOD AND DEVICE FOR DETERMINING THE HYDRATION, FITNESS AND NUTRITION STATUS OF A HUMAN BODY

CROSS REFERENCE TO RELATED APPLICATIONS

This application is a U.S. National Stage Entry of International PCT Application No. PCT/IB2018/000319, filed Apr. 4, 2018 which claims the benefit of U.S. Provisional Application No. 62/481,378 filed Apr. 4, 2017, the entire contents of which are hereby incorporated herein by reference in their entirety.

BACKGROUND

The invention relates to a method of determining the hydration, fitness and nutrition status of a human body in vivo, and to a device for performing the steps of the method. The invention further relates to the field of bioelectric impedance spectroscopy and to the field of three or more compartment models The human body consists principally of water, fat, bone, and protein. Water is the largest component amounting to typically about 60% of the total body weight (W). The total body water (TBW) is contained in an intracellular water (ICW) space surrounded by semi-permeable cell membranes, and an extracellular water (ECW) space that includes both tissue and vascular water. The intracellular water (ICW) compartment relates to a nutritional status as it reflects the size of exchangeable protein stores and the body's metabolic cellular mass performing all work and consuming all oxygen. It is known that intracellular water (ICW) generally maintains a 70% relationship to a total cell volume. Protein and glycogen make up most of the remainder. The extracellular water (ECW) is thought to principally reflect hydration status.

The human body contains adipose tissue and lean tissue. The adipose tissue (AT) is composed lipid (fat), and roughly 5% mineral-protein and 20% water, with roughly 13% extracellular water (ECW) and 7% intracellular water (ICW). The lean tissue (LT) consists of water, protein and bone mineral. Healthy adipose-free lean tissue contains roughly 73% of water of which about 46% is intracellular water (ICW) and about 27% is extracellular water (ECW). The intravascular water is roughly 15% of extracellular water (ECW). The total body water (TBW) is the sum of extracellular water (ECW) and intracellular water (ICW).

The status of intracellular water (ICW) and the extracellular water (ECW) are primary biomarkers of health and disease because the disease process may often result in an increase of extracellular water (ECW) and a loss in intracellular water (ICW), e.g., a decomposition of muscle tissue. Diseases of the heart, kidney, liver, or diabetes and obesity are known to cause such changes. There is also a disadvantageous, mutually reinforcing relation between overhydration, hypertension and heart or kidney disease progression.

In health, a large volume fraction of intracellular water (ICW) reflects a muscle mass that is protective of insulin resistance, strength, physical function and higher metabolic activity. Hence, in health overhydration is less of concern, but avoiding dehydration ensures physical performance, mental cognition and reduces stress on the vital tissues.

Because body water is conductive and the ICW is separated from the ECW by a capacitive cell membrane, the ICW and ECW compartments can be measured using a bioelectric impedance spectroscopy (BIS) technique. With 2 to 4 or even more electrodes attached to the subject, the complex impedance measured over spectrum of frequencies, e.g., from 5 kHz to 1 MHz, is fit to a known mathematical model of biological tissue, separating the tissue into its components. In turn the results of such fit can be used to analyze the tissue and predict intracellular water (ICW) and the extracellular water (ECW) volumes, and lean and fat mass. The model most often used is the classic Cole-Cole model.

An impedance may be related to human body composition by employing a two-compartment (2C) model whereby the total body water (TBW) is considered to be a fixed fraction (e.g., 73%) of the body's fat-free mass (FFM), which is derived from TBW/0.73. In turn, body fat is determined by subtracting FFM from total body weight. This early concept is technology driven as the common dual energy x-ray absorptiometry method (DXA) can only estimate fat mass and all else is FFM including bone, which similarly true for the air and water displacement density methods, which predict a fraction of body fat mass. As with the impedance method, an isotope dilution method to determine total body water content may be used to derive the body's fat-free mass (FFM) by dividing TBW by, e.g., 0.73 and subtracting the result from total body weight in order to obtain the fat mass (FM). The above empirical methods are, however, expensive and unsuited for routine use. In contrast, bioelectric impedance spectroscopy (BIS) allows to determine both compartments, fat mass and fat-free mass via a measurement of the total body water (TBW) content with reasonable accuracy on healthy young adults.

Nevertheless, a 2C model (fat mass and fat-free mass) as described above is inadequate as normally hydrated adipose tissue (NH_AT) contains water that is distinct from the water associated with the more metabolically active normally hydrated lean tissue (NH_LT). Thus, variations in the fraction of normally hydrated adipose tissue (NH_AT), which may typically contain about 20% water, causes significant errors in estimating the more metabolically active lean tissue (NH_LT) compartment. Worse yet, the 2C model approach does not account for the dehydration and overhydration which often occurs during disease.

Document U.S. Pat. No. 7,072,710 B2 (Chamney) discloses a method for the determining a dry weight, i.e., a target normal hydration, to allow improving the fluid management in kidney dialysis therapy. An extracellular water volume (ECW) and a body weight of a patient at times (t) are determined using bioimpedance measurements. The dry weight of the patient is derived from an intersection of the corresponding function (EBW/W) with a previously (empirically) established extracellular water volume (ECW) against dry weight reference relation representing healthy subjects. However, this method may tend to overestimate the dry weight in subjects presenting a large fat-to-weight ratio. Moreover, according to this method, the relation between the extracellular water volume (ECW) and body weight (W) for normally hydrated subjects is considered to be proportional. However, this slope may actually vary significantly with the ratio of lean body tissue with respect to fat mass.

Document U.S. Pat. No. 7,133,716 B2 (Kramer & Chamney) discloses a method for determining a volume of extracellular water that forms a compartment of malhydration fluid in a patient. More specifically, a four-compartment (4C) model of the human body is set up in order to derive information on fluid status from extra- and intracellular volumes measured by bioimpedance spectroscopy. The model allows the determination of weights of each of the four compartments, namely said malhydration, and further fat, muscle and remaining 'basic' components, which includes bones, organs, blood and skin, etc. Thereby, extra- and intracellular water volumes are analyzed in different tissues of the body primarily based on empirical data.

The method comprises iteratively performed steps, wherein anthropometric data such as length and total body weight are first input to derive—based on the model and empirical data—the weight fractions of the remaining 'basic' components. Based on an assumption that fat tissue (adipose) mass neither comprises intracellular or extracellular water, and that the malhydration component also lacks intracellular water, the muscle mass is next derived applying the BIS technique to determine intracellular water (ICW) and assuming a fixed ratio between ECW and ICW in muscle tissue. Next, the malhydration component is derived as it is the only remaining compartment comprising extracellular water (ECW). Given the weights for the 'basic' compartment, the muscle compartment and the malhydration compartment, the fat mass be finally be determined as the difference between the sum of the three other compartments and measured total weight. It may be noted that above (incorrect) assumption that adipose tissue contains a-negligible amount of water, makes the method highly dependent upon percentage body fat.

Document U.S. Pat. No. 8,340,754 B2 (Chamney & Wabel) discloses a method of monitoring the hydration and/or nutrition status of a patient. A malhydration component, an adipose tissue component and a lean tissue component is derived by performing a bioelectric impedance spectroscopy (BIS) of the patient to obtain mass or volume fractions of total extracellular water (ECW) and total intracellular water (ICW) and measuring the total body weight (W) using a scale. In order to derive the three aforementioned components from the instantly measured and derived quantities, experimental reference data have previously been obtained via dilution techniques or dual X-ray absorptiometry (DXA). These reference data may be used to associate a measured quantity of total intracellular and extracellular water each with adipose and lean tissue. In turn, the masses of the desired components in the three-compartment (3C) model are derived that is set up according to this document.

Document U.S. Pat. No. 7,917,202 B2 (Chamney & Wabel) discloses a similar method in which it is taken account of errors in the fraction of intracellular water (ICW) introduced by a variation in normally hydrated adipose tissue (NH_AT). A model is proposed that considers the body as two distinct lean and adipose tissues and allows the intracellular water (ICW) resistivity calculation to "float" according to the ratio between adipose tissue (NH_AT) mass and lean tissue (NH_LT) mass.

In document Chamney et al. ("A whole-body model to distinguish excess fluid from the hydration of major body tissues", Am. J. Clin. Nutr. 2007, Vol. 85, p. 80-89) the 3C compartment concept based on normally hydrated lean tissue (NH_LT) and normally hydrated adipose tissue (NH_AT) is further developed. It is stressed therein that it would be important that a corresponding model takes into account the different ratios of extracellular water (ECW) to intracellular water (ICW) each in normally hydrated lean tissue (NH_LT) and normally hydrated adipose tissue (NH_AT). Chamney et al. refers to the malhydration component as excess ECW (ExF).

A volume calculation with regard to intracellular water (ICW) and extracellular water (ECW) had been proposed in literature, e.g., in Moissl, U. M., Wabel P., Chamney P. W., Bosaeus I., Levin N. W., et al. (2006): "Body fluid volume determination via body composition spectroscopy in health and disease" in: Physiol. Meas. 27, 921-933. Those techniques are, however, known to be inaccurate for low body fat subjects.

SUMMARY OF THE INVENTION

It is an object to provide a method which improves the determination of the status of hydration in a human body, e.g., a patient. It is in particular an object to simplify the steps and/or to properly account for changes within constituent fluid fractions of the compartments involved.

The object is solved by a method according to claim 1. The object is further solved by a method according to claim 9. Still further, the object is solved by a device according to claim 11, by a computer program product according to claim 12, or by a computer-readable storage medium according to claims 13. Advantageous aspects are provided in the dependent claims.

According to embodiments, a method of determining a status of hydration and/or nutrition of tissues in a human body is provided wherein values are each of a mass or volume fraction of intracellular water (ICW) and a mass or volume fraction of extracellular water (ECW) of the human body. In some of the embodiments, the values may be obtained from bioelectric impedance spectroscopy measurements of a human body or similar measurement or determination methods. Such methods allow an efficient, less time consuming and in particular non-invasive measurement at the body of, e.g., the patient.

Further, a two-dimensional parameter space with a mass or volume fraction of intracellular water (ICW) and a mass or volume fraction of extracellular water (ECW) as separate parameters is defined. In practice, the parameter space may be represented or visualized by a plane and a coordinate system with mass or volume fractions as x- and y-axes. In that parameter space, a reference line is defined, which represents associated values for each of a mass or volume fraction of intracellular water (ICW) and a mass or volume fraction of extracellular water (ECW) of a number of healthy subjects. This line may be straight or linear within the parameter space. However, alternatives shall be encompassed wherein there is a non-linear relation between respective masses or volume fractions of ICW and ECW.

According to specific embodiments, empirical data may have been obtained previously, e.g. by dedicated and more precise experimental methods such as DXA, dilution methods and/or air or water displacement methods as described above. According to further specific embodiments, the line may have been obtained by applying a regression fit to the data, or by other statistical analysis of the data well known in the art.

Now, a position is located within the parameter space which corresponds to the associated values of the mass or volume fraction of intracellular water (ICW) and the mass or volume fraction of extracellular water (ECW) obtained with respect to the human body. The parameter space preferably is a metric space in a mathematical sense. Accordingly, a distance can be determined between the position and the reference line. Preferably, the distance is measured or evaluated between the located position (human body) and a nearest point on the reference line. In that case, and when the line is straight or linear, or continuously curved, the angle between the reference line at the position nearest to the located position and the direction of a corresponding distance vector is 90 degrees. However, different rules for defining the direction of distance measurement between the located point and the reference line may be applied as well, and an embodiment wherein the distance is measured along a shortest line of connection between the point and the line shall not be considered to limit scope of the appended claims.

One key issue is that it has been found that the determined distance from the line may serve as a new measure for an amount (mass or volume fraction) of the hydration (HYD) of a human body.

In other words, a compartment of hydration (HYD) of, e.g., the patient's body can be derived without applying any assumptions for splitting into fractions the masses or volume fractions of ICW and ECW with respect to each of normally hydrated lean tissue (NH_LT) and normally hydrated adipose tissue (NH_AT). Due to those "sub-compartments" in prior art, it turns out that assumptions, according to which all changes in hydration occur in the extracellular water (ECW) space, may not be correct, thus failing to account for the changes in intracellular water (ICW). Also significant dynamic changes in extracellular water (ECW) due to compartmental fluid shifts, or changes in ion, PH or temperature are not covered the models of prior art. The dynamic changes can be large. For example, removal of body water during dialysis may result in significant changes in intracellular water (ICW) that has yet not been accounted for. Existing prior art 3C models consisting of excess fluid (ExF), normally hydrated lean tissue (NH_LT) and normally hydrated adipose tissue (NH_AT) are found to yield erroneous changes in predicted fat mass in one day due to apparent intracellular water (ICW) fluid shifts. This phenomenon has recently been reported in dialysis where ionic induced osmotic pressure change caused significant variability in NH_LT and NH_AT pre and post dialysis, see Antonelou, M.; El-Kateb S.; Davies N.; Davenport A.: "Changes in serum osmotic pressure following haemodialysis treatments lead to changes in bioimpedance spectroscopy estimates of lean and adipose tissue" in European Journal of Clinical Nutrition 2017, Feb. 1. doi: 10.1038/ejcn.2016.270.

According to embodiments of the method, a 3C model is proposed wherein the body's three major compartments (3C) of normally hydrated lean tissue (NH_LT), normally hydrated adipose tissue (NH_AT) and hydration (HYD) may be predicted. In turn, body fat mass and muscle mass can be determined.

Further, a method according to further embodiments proposed herein minimizes the effects of dynamic variations in extracellular water (ECW) and intracellular water (ICW) on the determination of the more static body elements as provided by normally hydrated lean tissue (NH_LT), normally hydrated adipose tissue (NH_AT) and hydration (HYD) status. In this case, we also consider hydration status (HYD) to be nearly static because this way we isolate it from dynamic changes in amounts or volume fractions of extracellular water (ECW) and intracellular water (ICW) due to fluid shifts, and to changes in ion, PH and temperature, as well as to changes due to measurement errors, changes in body position and the like.

The more static part (which is herein denoted as "baseline") is separated from the dynamic part after the values for extracellular water (ECW) and intracellular water (ICW) have been determined. The distance from the reference line is calculated using the static variables only. Herein, amounts of extracellular water (ECW) and intracellular water (ICW) can be expressed as:

$$ECW = ECW_b + ECW_d, \quad (1)$$

$$ICW = ICW_b + ICW_d, \quad (2)$$

respectively.

Accordingly, in the setup of a 3-compartment model as described above, according to embodiments of the invention, only those more static baseline quantities $ECW_b$ and $ICW_b$ are considered to calculate the compartments normally hydrated lean tissue (NH_LT), normally hydrated adipose tissue (NH_AT) and hydration (HYD). According to a further refinement, $ECW_b$ and $ICW_b$ are obtained by averaging values of ECW and ICW determined over multiple, e.g., subsequent measurements, for example over a time interval or a predetermined number of subsequent measurements.

On the other hand, a full 5 compartment (5C) model can be setup according to further embodiments by taking advantage of the residual dynamic components $ECW_d$ and $ICW_d$, both of them now being treated as two further separate compartments.

Hence, the method according to these embodiments is considered to dramatically improve the practice and utility of bioelectric impedance spectroscopy (BIS) measurements for estimating a human body's fat and muscle condition. On the other hand separating the dynamics changes from the static measures provides new and powerful uses for determining hydration, training, energy, overtraining and injury recovery status.

It is noted that according to further embodiments of the invention, the setting up of a parameter space or plane, the determination of a reference line within that space or plane, and the calculation of a distance from the located point (which reflects, e.g., the subjects' values for ECW and ICW) may be cast into a simple linear equation (when the reference line itself is linear), which can be expressed as $$HYD(ICW_p, ECW_p) = f \cdot ICW_p + g \cdot ECW_p + h \quad (3)$$

wherein linear coefficients f, g, and h are determined from a fit to previously obtained experimental data of healthy and optionally also diseased patients wherein the hydration index (HYD) is a mass or volume fraction of a hydration (HYD), and wherein $ICW_p$, $ECW_p$ denote intracellular and extracellular water fractions. The hydration index (HYD) reflects over—as well as dehydration with respect to normal hydration.

According to embodiments of the method, the hydration index (HYD) is calculated from baseline volumes ($ECW_b$, $ICW_b$) and therefore quantifies the average of the subject hydration status. From the same baseline volumes ($ECW_b$, $ICW_b$) expressed as percent mass or volume fractions, the fat free mass (FFM) may be calculated according an equation known from literature:

$$FFM = d_{ECW} * ECW_b + d_{ICW} * ICW_b. \quad (4)$$

wherein $d_{ECW}$ and $d_{ICW}$ are the densities of respective extracellular and intracellular fluids and associated materials, and $ECW_b$ and $ICW_b$ are respective volume fractions in units [%]. Then, body fat mass is calculated by subtracting the fat free mass (FFM) from total body weight. Further, a normally hydrated adipose tissue (NH_AT) may be calculated by dividing body fat mass by, e.g., 0.75 according to known constants in literature. Therefore, normally hydrated lean tissue (NH_AT) is calculated by subtracting normally hydrated adipose tissue (NH_AT) and hydration status (HYD) from total body weight:

$$NH\_LT = W - NH\_AT - HYD \quad (5)$$

According to even further embodiments, a connection of electrodes on individual limbs enables the measurement of the impedance of different body segment such as arms, legs, trunk, etc. Modified volume calculation methods are provided herein for the purpose of calculating ICW and ECW for individual segments. A model for the determination of segment mass based on height and weight is developed in order to apply the same relations developed for the total body as described above and in the detailed embodiments also to individual body segments.

According to a further aspect, a method for setting up a set of volume model equations for use in determining the hydration, fitness and/or nutrition status of a human body, or of segments of the human body is provided includes the steps:

defining a sample of multiple subjects, and for each of the subjects:
calculating (STEP1) a mass or volume fraction of extracellular water ($ECW_1$) and of intracellular water ($ICW_1$), respectively, using a set of first volume model equations,
calculating (STEP2) each a first value of a mass or volume fraction of hydration ($HYD_1$, $HYD_2$), a predicted body fat mass or volume fraction ($BF_1$), and a normally hydrated lean tissue mass or volume fraction ($NH\_LT_1$) of a 3C compartment model, based on the mass or volume fraction of intracellular water ($ICW_1$) and the mass or volume fraction of extracellular water ($ECW_1$),
determining each a second value of a body fat mass or volume fraction ($BF_2$) from experimental results,
replacing the first value of the predicted body fat mass or volume fraction ($BF$) with the second value of body fat mass or volume fraction ($BF_2$) to correct for an prediction errors of body fat,
adjusting (STEP3) the normally hydrated lean tissue mass or volume fraction ($NH\_LT_2$) in response to the corrected body fat mass ($BF_2$),
adjusting (STEP 4) the mass or volume fraction of extracellular water ($ECW_2$) and of intracellular water ($ICW_2$), respectively; and
setting up a set of second volume model equations each for determining the mass or volume fraction of extracellular water ($ECW_2$) and of intracellular water ($ICW_2$), respectively,
determining coefficients in the second volume model equations by a regression or fit of the second volume model equations to experimental data for each of the subjects with respect to measured values each of a mass or volume fraction of extracellular water (ECW) and of intracellular water (ICW).

The set of second volume equations may thereby be expressed as:

$$ECW_{DXA-opt}=a_0+a_1 \cdot W+a_2 \cdot H+a_3 \cdot R_e^{-2/3}+a_4 \cdot R_i^{-2/3}+a_5 \cdot H/W+a_6 \cdot W/H, \text{ and}$$

$$ICW_{DXA-opt}=b_0+b_1 \cdot W+b_2 \cdot H+b_3 \cdot Re^{-2/3}+b_4 \cdot Ri^{-2/3}+b_5 \cdot H/W+b_6 \cdot W/H,$$

wherein the coefficients $a_0$, $a_1$, $a_2$, $a_3$, $a_4$, $a_5$, $a_6$ are obtained by a first fit to the experimental data, and the coefficients $b_0$, $b_1$, $b_2$, $b_3$, $b_4$, $b_5$, $b_6$ are obtained by a second fit to the experimental data.

According to a further aspect, a method is provided for determining the hydration, fitness and/or nutrition status of a human body, or of segments of the human body, comprising:

providing values each of mass or volume, or a mass or volume fraction of intracellular water ($ICW_P$) and a mass or volume, or mass or volume fraction of extracellular water ($ECW_P$) of the human body or the segment;
deriving a mass or volume, or a mass or volume fraction, of hydration (HYD) from the provided values.
calculating a body fat mass (BF) by subtracting the mass or volume, or a mass or volume fraction of intracellular water (ICW) and associated materials and the mass or volume, or a mass or volume fraction of extracellular water (ECW) and associated materials from the total body weight (W), respectively,
calculating a mass or volume fraction of a normally hydrated adipose tissue (NH_AT) by dividing the body fat mass with a factor $\vartheta$ accounting for water and associated materials in adipose tissue, wherein $\vartheta$ is selected between 0.70 and 0.90, preferably between 0.73 and 0.77, and most preferable at or around 0.75,
calculating a mass or volume fraction of a normally hydrated lean tissue mass (NH_LT) by subtracting the mass or volume fraction of a normally hydrated adipose tissue (NH_AT) and mass or volume fraction, of hydration (HYD) from total body weight, respectively.

According to a further aspect, a method is provided for determining the hydration, fitness and/or nutrition status of a human body, or of segments of the human body, comprising:

providing values each of a mass or volume fraction of intracellular water ($ICW_P$) and a mass or volume fraction of extracellular water ($ECW_P$) of the human body or the segment;
wherein the step of providing values each of a mass or volume fraction of intracellular water ($ICW_P$) and a mass or volume fraction of extracellular water ($ECW_P$) of the human body are repeated a number (N) of times,
wherein, by means of averaging, or filtering, or a Fourier transformation with regard to time, the mass or volume fraction of intracellular water (ICW) and the mass or volume fraction of extracellular water (ECW) and the weight (W) are separated into:
(i) a static or nearly static baseline component of mass or volume fraction of intracellular water ($ICW_B$) and mass or volume fraction of extracellular water ($ECW_B$) and weight ($W_B$), and
(ii) a dynamically changing component of mass or volume fraction of intracellular water ($ICW_D$) and mass or volume fraction of extracellular water ($ECW_D$) and weight ($W_D$), wherein:

$$ICW=ICW_B+ICW_d$$

$$ECW=ECW_B+ECW_d$$

$$w=w_B+w_d$$

Herein, steps of:
deriving a mass or volume, or a mass or volume fraction of hydration (HYD) based on the static or nearly static baseline component of mass or volume fraction of intracellular water ($ICW_B$) and mass or volume fraction of extracellular water ($ECW_B$) and weight ($W_B$) only;
determining a body fat mass (BF) and/or a normally hydrated adipose tissue mass (NH_AT) from static or nearly static baseline component of mass or volume fraction of intracellular water ($ICW_B$) and mass or volume fraction of extracellular water ($ECW_B$) and, weight ($W_B$) only;

determining a normally hydrated lean tissue mass (NH_LT) from the mass or volume fraction of hydration (HYD) and the normally hydrated adipose tissue mass (NH_AT);

may be performed wherein:
(a) the dynamically changing component of mass or volume fraction of intracellular water ($ICW_D$),
(b) the dynamically changing component of mass or volume fraction of extracellular water ($ECW_D$),
(c) the hydration index (HYD),
(d) the normally hydrated lean tissue mass (NH_LT), and
(e) the normally hydrated adipose tissue mass (NH_AT)

form a 5 compartment (5C) model.

Throughout this document, compartments or body portions (e.g., normally hydrated lean tissue, normally hydrated adipose tissue, body fat, hydration, extracellular water, intracellular water, muscle mass or volume, fat free mass or volume, total body weight or volume, etc.) are described in terms of (absolute) masses or volumes, or of mass fractions or volume fractions, respectively, each alone or in combination. It is to be understood, however, that where a mass fraction or a volume fraction etc. is denoted, the respective other quantity is encompassed herein as well where appropriate.

BRIEF DESCRIPTION OF THE DRAWINGS:

Further features and advantages of the invention will become apparent from the description of embodiments by means of the accompanying drawings. In the drawings.

Figure 1:
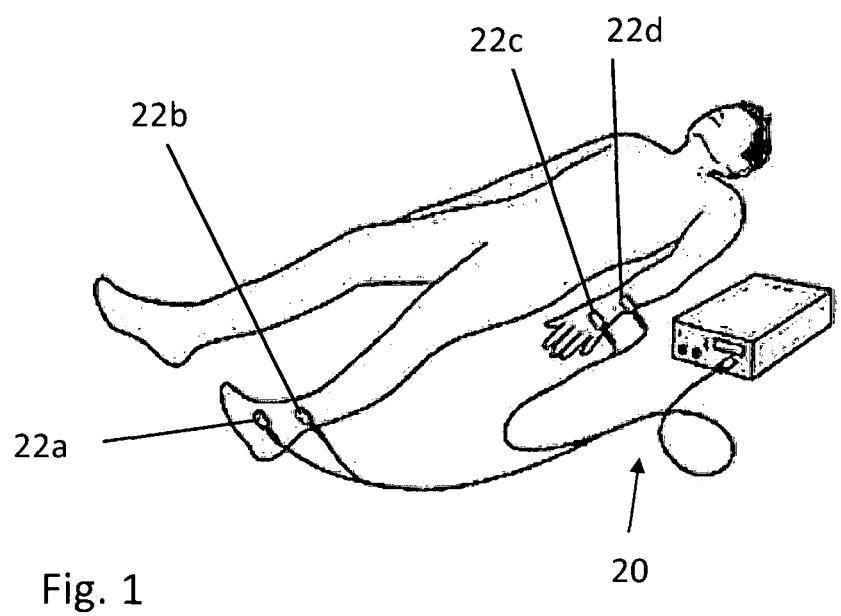
FIG. 1 shows in a schematic view a supine wrist-ankle (whole body) bioelectric impedance spectroscopy measurement (BIS)

DETAILED DESCRIPTION OF EMBODIMENTS:

An embodiment is described with reference to FIGS. 1 through 11. FIG. 1 reveals an outline of a bioelectric impedance spectroscopy (BIS) measurement as used in connection with this embodiment. A BIS measurement unit 20 is arranged with a set of four electrodes 22a, 22b, 22c, 22d which are non-invasively attached (e.g., adhesively) to the surface of the skin of a human body at the wrist and ankle, respectively. This measurement enables total body volume to be determined. In addition, using two pairs of electrodes on different body segments allows to more appropriately consider the volumes of respective body portions (e.g., legs, arms, etc.) in the evaluation steps of the BIS measurement. The measurement is generally performed in a supine posture of the human body. It is noted that according to alternative embodiments standing positions or other postures are conceivable and the scope is not limited by the specific posture of the human body during BIS measurements.

An alternating current/voltage with varying frequency from, e.g., 5 kHz to 1 MHz is applied to the electrodes 22a-d and the complex impedance, i.e., resistance and reactance is measured using techniques well known in the art, described for example in Xitron Hydra ECF/ICF (Model 4200) Bio-impedance spectrum analyzer, Issue 1.01 6/97 (1997), Operating Manual Revision 1.01 Xitron Technologies Inc.: San Diego, USA. It is noted that other limits than 5 kHz and 1 MHz may be applied as well, for example 1 kHz and 500 kHz etc., and also the frequency intervals for each single measurement may be defined depending on the specific needs.

Figure 2:
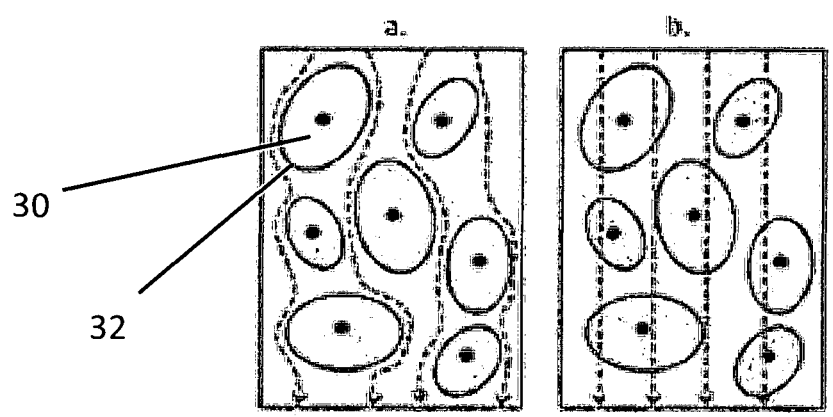
FIG. 2 shows a schematic example of low frequency electrical current flowing around biological cells in solely the extracellular water (a) and high frequency currents conducting through both the extracellular water and intracellular water (b)
Figure 4:
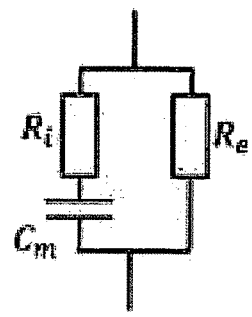
FIG. 4 shows a simplified circuit diagram of an electrical circuit indicative of the frequency response observed.

FIG. 2 shows in a schematic cross section of cell tissue the principles of a BIS measurement. The cell tissue is herein represented by cells 30 bound by cell membranes 32 and filled with intracellular water ICW, while being surrounded by extracellular water ECW. Electrical current flows through the respective fluids in the tissue, wherein the flow can be separated into two parts: a first part that flows through extracellular water which surrounds the cells. In this flow of electrical current, basically only a real part of the impedance is observed as the resistance $R_e$ of the extracellular water column determines circuit characteristics. A second part directly flows through the cells via cell membrane in and out of the cell and through the intracellular and extracellular water, respectively. Since the cell membrane acts like a capacitor $C_m$ not admitting a flow of a static direct current, a complex contribution arises when an alternating frequency is applied, in addition to a real part resistance $R_i$ of the intracellular water. An equivalent circuit diagram including resistors and capacitors is shown in FIG. 4.

Figure 3A:
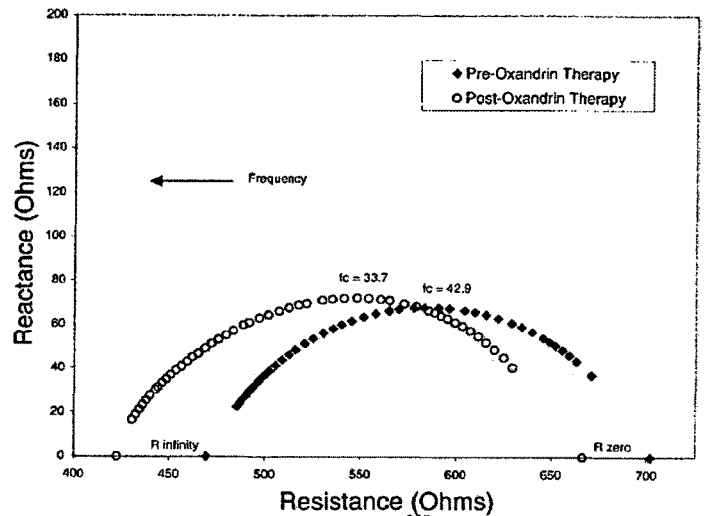
FIG. 3a shows a representative Cole model plot of resistance vs. reactance (X) measured on one subject pre- and post-Oxandrin therapy (a synthetic, oral active anabolic-androgenic steroid), wherein $R_0$ and $R_{inf}$ were derived from a modeling fit, and the characteristic frequency (fc) is the frequency of maximum X.
Figure 3B:
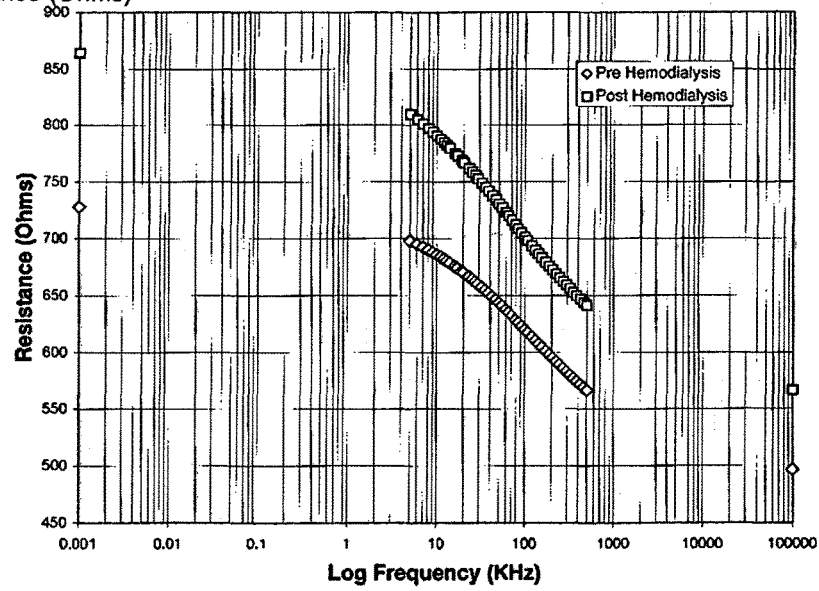
FIG. 3b shows a diagram with frequency plotted versus resistance as measured on one patient before and after hemodialysis, wherein $R_0$ and $R_{inf}$ are represented at 0.001 Hz and 100,000 KHz, respectively, and wherein $R_0$ and $R_{inf}$ were derived from modeling.

FIG. 3a shows a Cole model plot wherein measured values of resistance are plotted versus reactance in a patient prior to and after an Oxandrin therapy, revealing the well-known semicircular relationship in both cases. As mentioned at very low frequencies there is little capacitive effect and the current flows almost only around the cells in the extracellular water ECW. In contrast, at very high frequencies, the influence of the capacitor $C_m$ becomes minimum and the current flows freely through both the extracellular ECW and intracellular water ICW. It is the objective is to separate ECW from ICW for an independent analysis. Since it is not technically possible to measure at a low enough or high enough frequency such as to directly obtain $R_e$ and $R_i$, the data are computationally extrapolated to the zero and infinite frequencies. At zero, only the contribution of $R_e$ from extracellular water ECW is measured. Hereby, the circuit is purely resistive ($R_0=R_e$).

Likewise, at the infinite frequency, the intracellular water ICW is fully included in the current path and in the measurement along with the contribution of extracellular water ECW. As it is clearly visible in FIG. 3b, the contribution from ICW measured is considerable at the measured low frequency (5 KHz) and where ICW is fully measured is far from the highest frequency measured (500 KHz).

The occurrence of a semicircle in a Cole model plot indicates that the measurement is conforming to theory. Because there may occur differences between the measured resistances and a corresponding theoretical model equation, measured data are fit to the model using common mathematical modeling fitting techniques. FIG. 3 shows a resulting model fit to a Cole model plot where data have been fit to determine frequency limits $R_0$ and $R_{inf}$. In order to derive the real part resistance $R_i$ of the intracellular water ICW, the respective electrical conductances have to be subtracted as follows:

$$1/R_i = 1/R_{inf} - 1/R_0 \qquad (6)$$

Now that the resistances $R_i$ and $R_0=R_e$ have been derived, further measurement data are obtained from the human body by measuring the body height H and the total body weight W in a further step using a scale and a metering device, for example. These data may also be provided from a database etc. instead of from direct measurement, if these data have been obtained elsewhere.

The parameters thus derived, i.e., ($R_i$, $R_0=R_e$, H and W) for the human body, are then used to calculate (predict) volumes of extracellular water (ECW) and intracellular water (ICW), respectively. According to this embodiment, equations as presented in Moissl, U. M., Wabel P., Chamney P. W., Bosaeus I., Levin N. W., et al. (2006): "Body fluid volume determination via body composition spectroscopy in health and disease" in: Physiol. Meas. 27, 921-933 for volumes of extracellular water (ECW) and intracellular water (ICW), respectively, are employed.

The equations are based on the well-known Xitron/Hanai equations (for ECW, see, e.g., Xitron Hydra ECF/ICF (Model 4200) Bioimpedance spectrum analyzer, Issue 1.01 6/97 (1997), Operating Manual Revision 1.01 Xitron Technologies Inc.: San Diego, USA) and an equation for ICW derived in Matthie, J. R.: "Second generation mixture theory equation for estimating intracellular water using bioimpedance spectroscopy", J. Appl. Physiol. 99, 780-1 (2005). However, those equations have been additionally corrected in Moissl et al. (2006) to account for the body mass index BMI considered to play an important role in the empirical data (BMI:=W/H$^2$):

$$ECW_{BCS} = k_{ECW} \left( \frac{H^2 \cdot \sqrt{W}}{R_0} \right)^{2/3} \text{ with } k_{ECW} = \frac{a}{BMI} + b \qquad (7)$$

wherein the coefficients a and b are determined by a regression fit of BMI to previously obtained experimental data of $k_{ECW}$.

$$ICW_{BCS} = k_{ICW} \left( \frac{H^2 \cdot \sqrt{W}}{R_1} \right)^{2/3} \text{ with } k_{ICW} = \frac{c}{BMI} + d \qquad (8)$$

wherein the coefficients c and d are determined by a regression fit of BMI to previously experimental data of $k_{ICW}$.

Particularly with respect to ICW, experimental data revealed a further dependence of coefficient $k_{ICW}$ on BMI index in Moissl et al. (2006). The equations are denoted as body composition spectroscopy (BCS) to distinguish them from those used in the Xitron Hydra 4200, Xitron Technologies, device. In the study of Moissl et al. (2006), the coefficients have been fit to the data yielding a=0.188, b=0.2883, c=5.8758, and d=0.4194. The fits were obtained by cross validation of data using 152 subjects, of which 120 were healthy and 32 dialysis patients. Of course, further analysis or investigation may yield differing fit results for these coefficients. Nevertheless, for the purpose of the embodiment, the coefficients as determined above are employed.

The values for the volume fractions of intracellular water ICW and extracellular water ECW obtained by computationally solving the above BCS (Moissl et al. (2006): "body composition spectroscopy") equations are then stored as values $ICW_P$ and $ECW_P$ in a memory.

Figure 5:
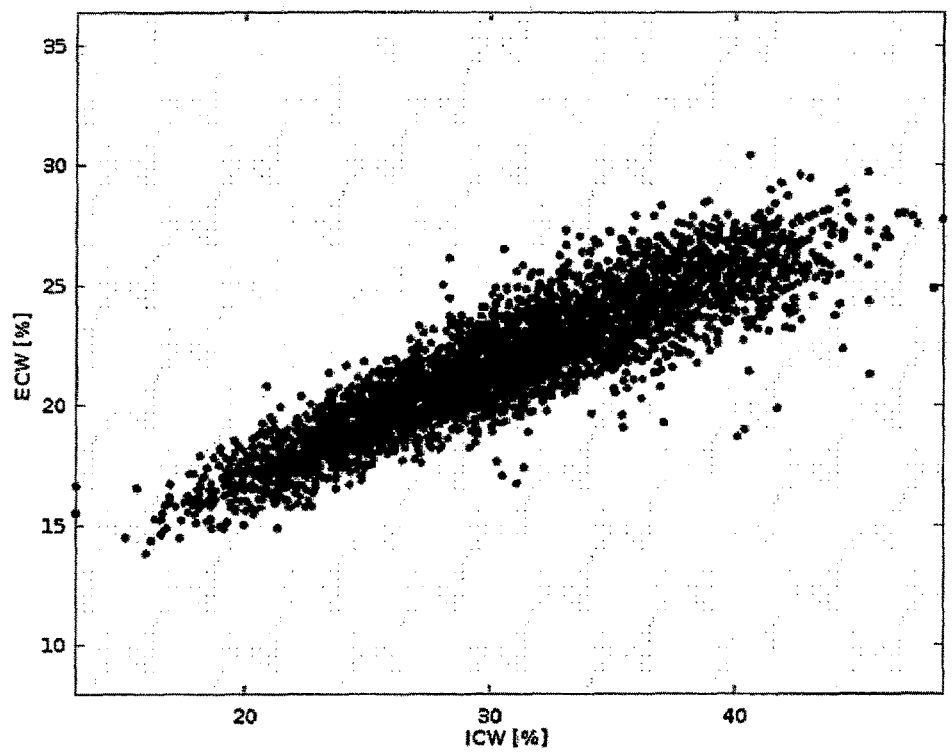
FIG. 5 shows a diagram of a parameter space (plane) indicating intracellular water (ICW) and extracellular water (ECW) normalized to body weight (in units of %) as parameters, wherein each dot represents a BIS measurement of a large number of subjects considered healthy.

Next, volumes fractions each of intracellular water ICW and extracellular water ECW are selected as two parameters ("ICW %", "ECW %") defining a two-dimensional parameter space or plane. In a preparation step of the method of the embodiment disclosed herein, data regarding volumes fractions each of intracellular water and extracellular water ECW were taken from a comprehensive database containing a large number of healthy subjects. This database is from the US National Health and Examination Survey (NHANES)

and the size of the sample is 3,010 people. The associated values of volume fractions of intracellular water ICW and extracellular water ECW may be plotted in the parameter space ("ICW %", "ECW %") for illustrative purposes as shown in FIG. 5.

The NHANES database provides BIS and DXA measurements on 3010 subjects, i.e., measurements of $R_e$ and $R_i$ obtained via BIS as well as accurate fat mass via DXA. By applying the developed modeling to the BIS data using the above Moissl et al. (2006) equations body fat errors can be calculated with respect to the DXA data computed body fat. It has been observed that Moissl et al. (2006) volume equations may tend to under-predict body fat on low body fat subjects. In other words reported values for body fat using extracellular water (ECW) and intracellular water (ICW) are lower than the corresponding DXA results. It has also been observed that for some subjects negative body fat can be reported, see also Berstad P., Randby A., Seim Ekeland G., Ulveland H., Omland T., Almendingen K.: "Body fat and fat-free mass measured by bioelectric impedance spectroscopy and dual-energy X-ray absorptiometry in obese and non-obese adults" in the British Journal of Nutrition (2012), April; 107(8):1192-200. A correction method is introduced (see in particular embodiment of calculation method (b) explained below) that improves the volume calculation and thus body fat prediction. The method is based on volumes obtained through regression by correcting ECW and ICW for DXA body fat.

Figure 6:
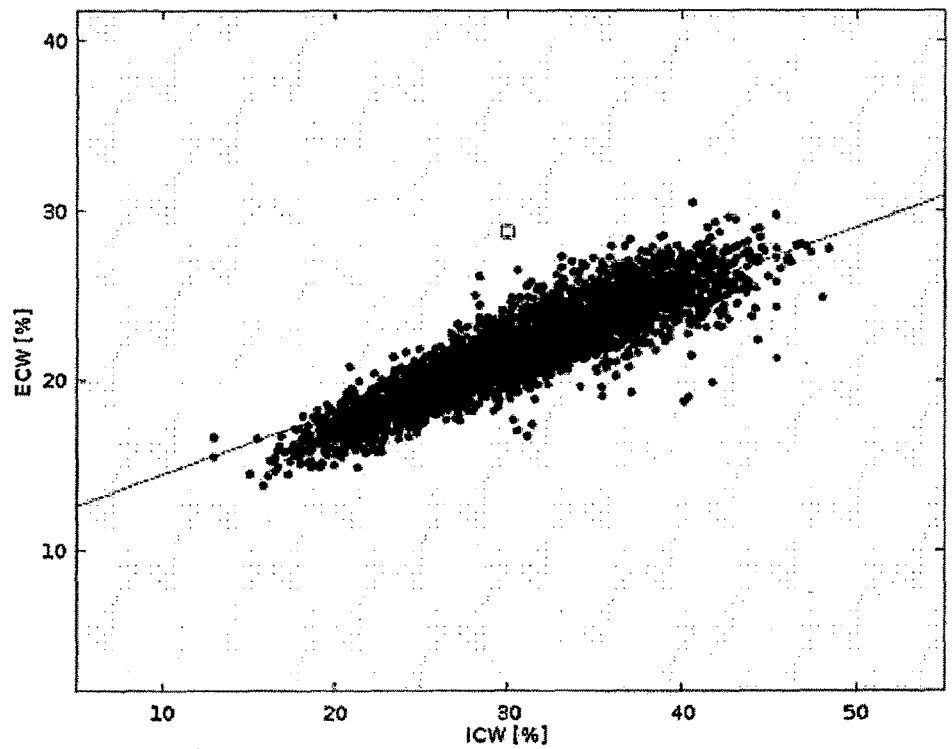
FIG. 6 shows the diagram of FIG. 5, wherein (a) a regression line (reference line obtained from linear regression, e.g. least squares fit) has been determined that represents the experimentally measured healthy subjects with normal hydration levels, (b) a point (indicated by a square that represents the mean intermediate water excess for a group of subjects reported in literature, Barac-Nieto et al., 1978) is located in the plane wherein the parameter values are obtained from uncorrected Moissl BIS volume calculations of a human body, and (c) a distance of the point from the reference line is determined indicating the level of overhydration or dehydration.

When ICW % and ECW % are plotted a clear correlation trend is visible in FIG. 6, and by means of regression (e.g., best fit or in particular least squares fit), a reference line may derived from these data, which line is taken to be representative of the associated values for each of a mass or volume fraction of intracellular water (ICW) and a mass or volume fraction of extracellular water (ECW) of a number of subjects considered healthy. "Healthy" herein means human bodies with normal hydration levels. The reference line is added to the diagram in FIG. 6. The dots shown for the NHANES sample of 3.010 healthy subjects are again depicted in this diagram for illustrative purposes only. The reference line in this embodiment is linear, and coefficients of this linear function (e.g., ICW as a function of ECW or vice versa) derived in the fit may be stored in the memory.

Next, as also shown in FIG. 6, the stored results of the human body of intracellular water $ICW_P$ [in units of %] (as a proportion of the entire body mass) and extracellular water $ECW_P$ [in units of %] are read out from memory and provided as coordinates to locate a corresponding point in the parameter space or plane (ICW % ECW %).

Next, as indicated by the square in FIG. 6, a distance is determined between the located point (indicated by a square in FIG. 6) representing the results for the concrete human body and the reference line representing the sample of healthy subjects. In this embodiment, the distance is a length of a straight line connecting the located point and the reference line, wherein that straight line is selected which has the shortest length. In other words, herein a direction in which the distance is measured is perpendicular to the linear reference line. It is noted that this scheme is not mandatory and other rules may apply in other embodiments, if it is found that the located point for the human body has to be related to another point on the reference line.

It has been found in studies by the inventors, that a rectangular distance within the parameter space or plane (ICW %, ECW %) regarding a point of a concrete human body from the normal or reference line is proportional to the body hydration index (HYD) and may be defined as:

$$\text{HYD}(ICW_P, ECW_P) = f \cdot ICW_P + g \cdot ECW_P + h \quad (9)$$

wherein linear coefficients f, g, and h are determined from a fit to experimental data. $ICW_P$ and $ECW_P$ are concrete values of ICW, ECW for a specific human body or patient, i.e., a specific point in the plane. The hydration index (HYD) represents the mass or volume fraction with respect to the total body weight (W), e.g., in units of percent. For each point in the parameter space or plane, the hydration index may be calculated using above formula. In other words, in an embodiment where once the equation have been derived and the coefficients are determined in a fit to experimental data, the provision of data ($R_i$, $R_0=R_e$, H and W) for the human body suffices to calculate $ECW_P$ and $ICW_P$ and then to apply the equation to finally arrive at the hydration index for this human body HYD ($ICW_P$, $ECW_P$). The plotting of experimental data, reference lines and located points of the human body in the plane and graphic output on a device such as a screen or printer may herein serve for illustrative purposes only. The above equation simply reflects the steps taken to derive the distance between a human body's associated values of $ICW_P$, $ECW_P$ and a normal or reference line reflecting a status of normal hydration.

The experimental data have been taken from a paper published in Barac-Nieto, M., Spurr, G. B., Lotero, H. and Maksud, M. G.: "Body Composition in Chronic undernutrition" in: The America Journal of Clinical Nutrition 31, 23-40 (1978), see in particular table 8 therein, and include a number (49 adult male subjects) of subjects with significant overhydration due to malnourishment. The data for that sample may also be plotted in the parameter space (in the drawings omitted for intelligibility purposes of the drawings).

Figure 7:
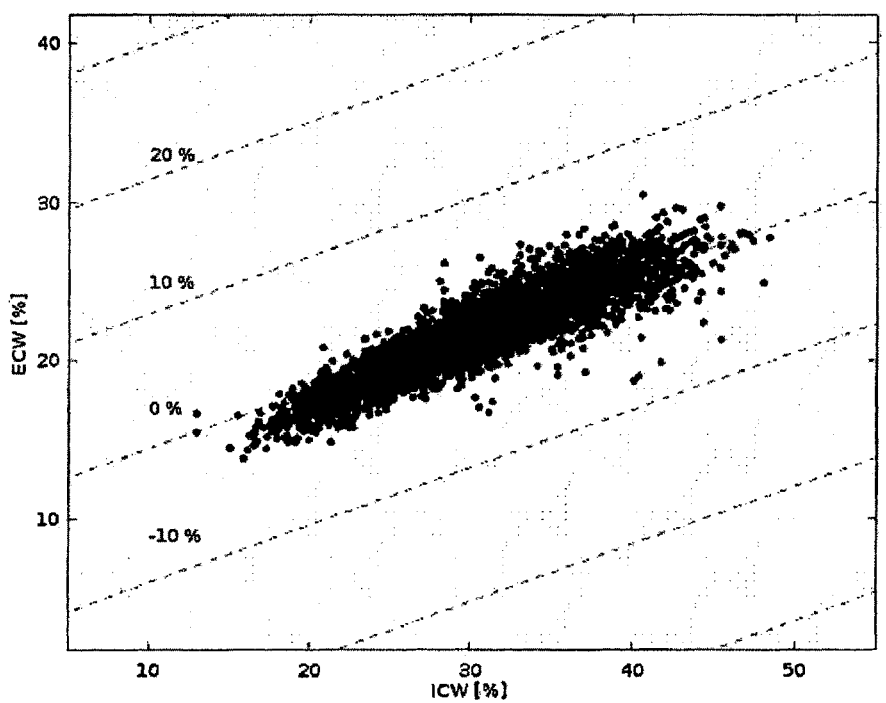
FIG. 7 shows the diagram of FIG. 5, wherein a function equation (HYD (ICW, ECW)=f·ICW+g·ECW+h) obtained from the empirical data indicates percentage of body hydration (dehydration yields negative values)
Figure 8:
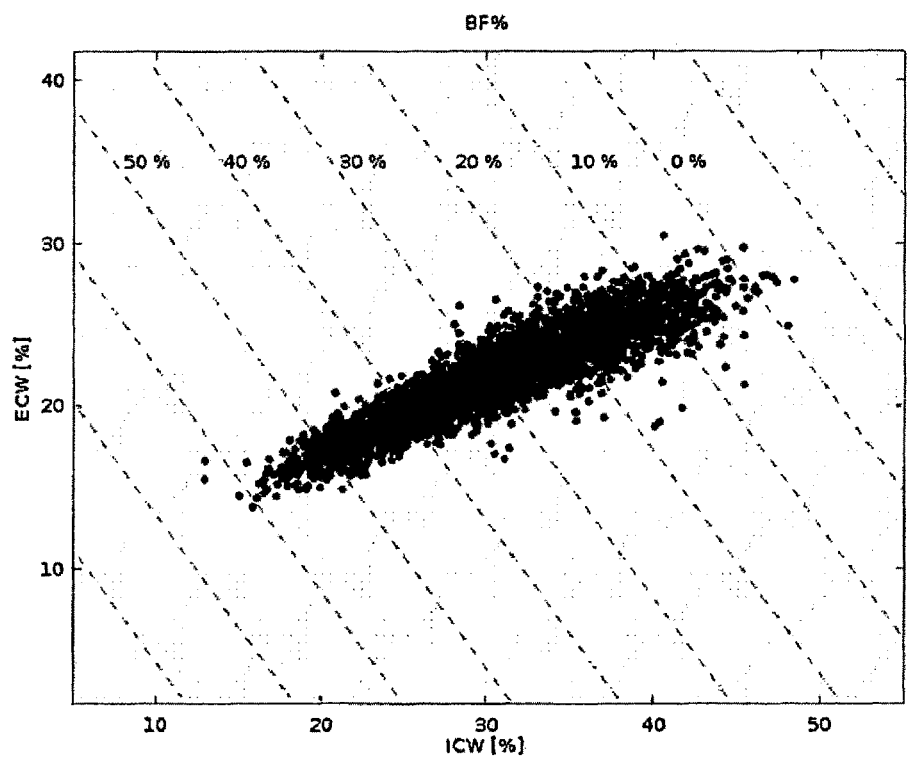
FIG. 8 shows the diagram of FIG. 5, wherein a body fat mass (BF, in units of %) has been calculated by subtracting from the measured (BIS) volume fractions of ECW and ICW and associated materials converted to mass fractions from body weight.
Figure 9:
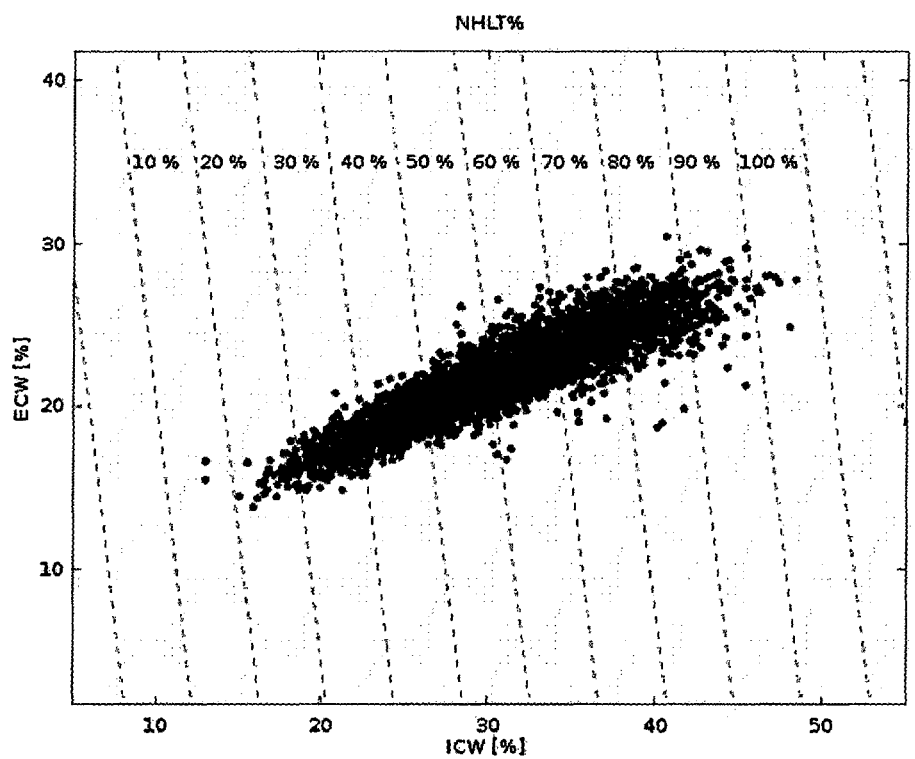
FIG. 9 shows the diagram of FIG. 5, wherein normally hydrated lean tissue (NH_LT) mass has been calculated by subtracting the hydration status (HYD) and normally hydrated adipose tissue (NH_AT) mass from the total body weight, and is expressed as levels of same percentage.

FIG. 7 displays the results obtained for each pair of parameter values ECW, ICW when solving the linear equation HYD ($ICW_P$, $ECW_P$)=f·$ICW_P$+g·$ECW_P$+h after the coefficients f, g and h have been fitted to the sample empirical data. The derived function HYD ($ICW_P$, $ECW_P$) indicates in FIG. 7 levels of same percentage of over hydration (dehydration yields negative values). Notably, positions in the parameter space occupied with same levels of the hydration index define lines parallel to the reference line. In other words, equation HYD ($ICW_P$, $ECW_P$)=f·$ICW_P$+g·$ECW_P$+h defines the reference line, where HYD ($ICW_P$, $ECW_P$)=0 denotes normal hydration. It may further be noted that negative values of the hydration index denotes dehydration.

In the next steps, the other 2 compartments of the instant 3C model according to this embodiment are calculated. Therein, the body fat mass of the concrete human body is calculated from the following equation (see L. H. Ellegård, M. Åhlén, U. Körner, K. G. Lundholm, L. D. Plank and I. G. Bosaeus; "Bioelectric impedance spectroscopy underestimates fat-free mass compared to dual energy X-ray absorptiometry in incurable cancer patients" in: European Journal of Clinical Nutrition (2009) 63, 794-801:

$$BF = 100 - (d_{ECW} \cdot ECW_P + d_{ICW} \cdot ICW_P) \quad (10)$$

This equation and constants $d_{ECW}$ and $d_{ICW}$ are known from literature. In the above paper Ellegård et al. (2009), $d_{ECW}$ denotes the mean density of extracellular water (ECW) and associated materials and amounts to 1,106 kg/l, while $d_{ICW}$ denotes the mean density of intracellular water (ICW) and associated materials and amounts to 1,521 kg/l. The results are displayed in FIG. 8.

It's known that body fat doesn't conduct electricity. Therefore the BIS volume impedance measurement does not account for fat volumes. Body fat is calculated by subtracting the detected conducting volumes (ICW and ECW and associated materials) converted to mass from the body weight (see below). Even if the body fat calculation method has historically been used in 2C models (Xitron), it is still valid for 3C modeling because it correctly reports body fat.

Furthermore, normally hydrated lean tissue (NH_AT) of the human body is calculated based on the following equation (in units of [%]):

$$NH\_LT=100\%-BF/0.75-HYD(ECW_P, ICW_P) \quad (11)$$

Figure 10:
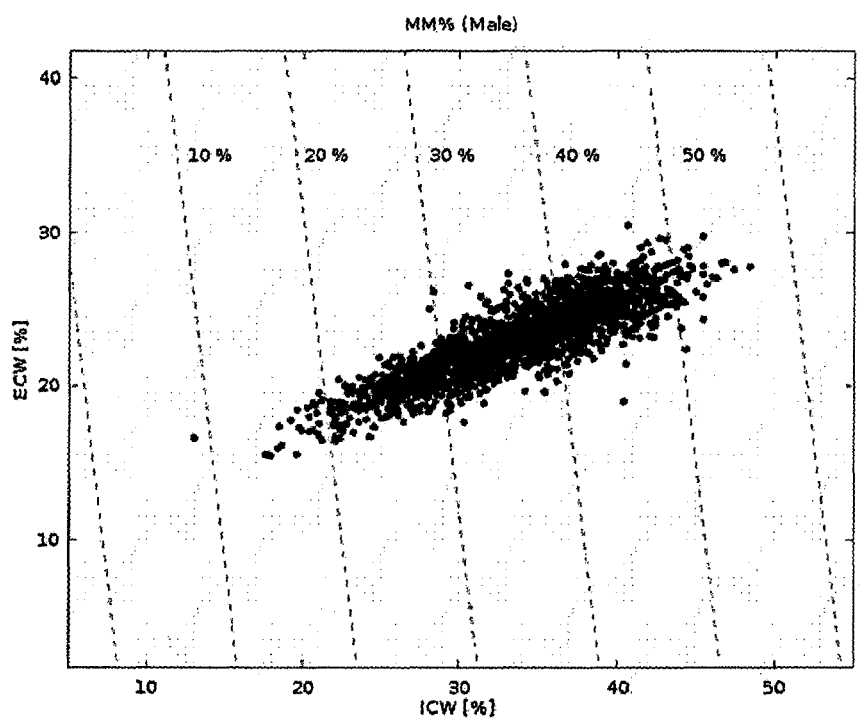
FIG. 10 shows the diagram of FIG. 8, wherein a muscle mass has been calculated from the normally hydrated lean tissue (NH_LT) for male subjects as, for example a fixed fraction of 53%.
Figure 11:
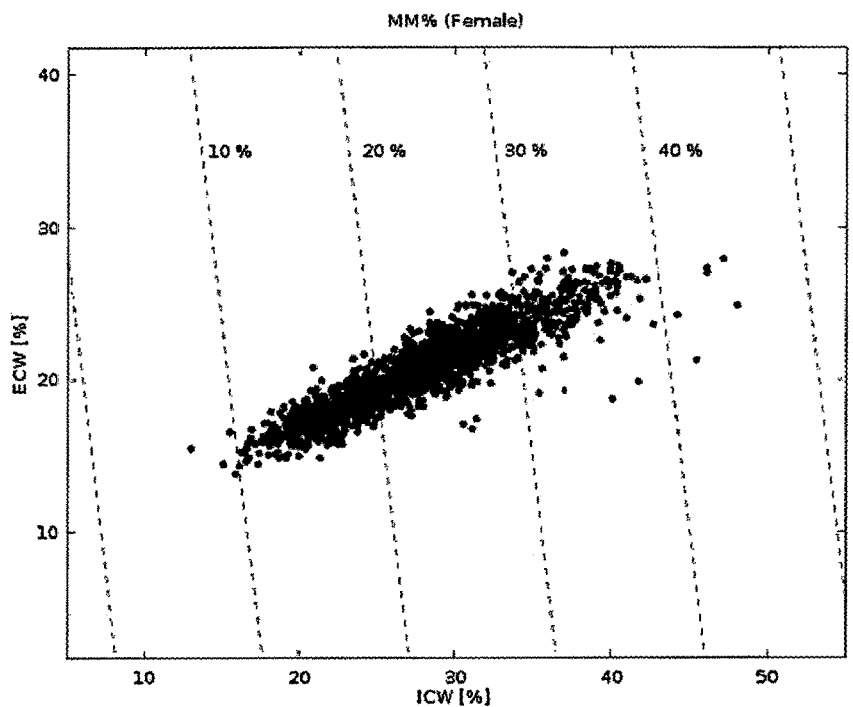
FIG. 11 shows the same as FIG. 10, but for female subjects, for example with a fixed fraction of 43%.

Therein, the term BF/0.75 corresponds to the ECW, ICW, and associated materials in normally hydrated adipose tissue (NH_AT). The results are displayed in FIG. 9. Furthermore, even the muscle mass (MM) of the concrete human body can be further calculated based on a fixed proportion of NH_AT, which is known from literature, namely, e.g., 53% for males and 43% for females. The results are shown in FIGS. 10 and 11, respectively.

In a more refined embodiment, the above described embodiment of a 3-compartment model may be extended to a 5-compartment model. Namely, in order to remove dynamic effects from the measurements, sequences of BIS-measurements of ECW and ICW of the same specific human body (p) are separated into two components called "baseline" (b) and "dynamic" (d):

$$ECW_p=ECW_b+ECW_d, \quad (12)$$

$$ICW_p=ICW_b+ICW_d, \quad (13)$$

Baseline components of $ICW_b$ and $ECW_b$ are thereby obtained by applying low pass filtering to subsequent ICW and ECW measurements. The baseline components may also be referred to as "more static". The residual dynamic $ICW_d$ and $ECW_d$ components represent changes in intracellular and extracellular compartments due to hydration changes and other factors including cell glycogen loading, response to training and others. These factors can be separately observed through the dynamic compartments $ICW_d$ and $ECW_d$.

From this point the baseline components $ICW_b$ and $ECW_b$ are now less sensitive to the described factor and may therefore be split into the other 3 compartments by calculating the difference from the reference line of normal hydration for determining the hydration (HYD), and Xitron density relation is used to calculate body fat (BF) and in turn the adipose tissue volume or mass fraction NH_AT. Finally, a volume or mass fraction of normally hydrated lean tissue (NH_LT) is calculated by subtracting NH_AT and HYD from total body weight W in the same manner as described above with respect to the first embodiment (i.e., a 3C model).

Figure 13:
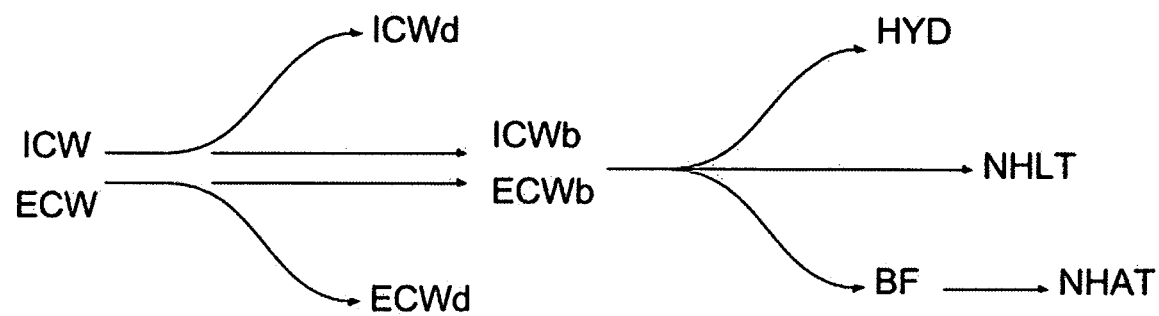
FIG. 13 shows an embodiment of a 5 compartment (5C) model scheme, which accounts for dynamic effects in bioimpedance spectroscopy measurements.

Next a 5C model is defined by the following compartments: $ICW_d$, $ECW_d$, HYD, NH_AT and NH_LT. Therefore, the effects resulting from the residual dynamic $ICW_d$ and $ECW_d$ components are taken into account. The setup of a 5-compartment model according to such an embodiment is shown in FIGS. 13.

Figure 14:
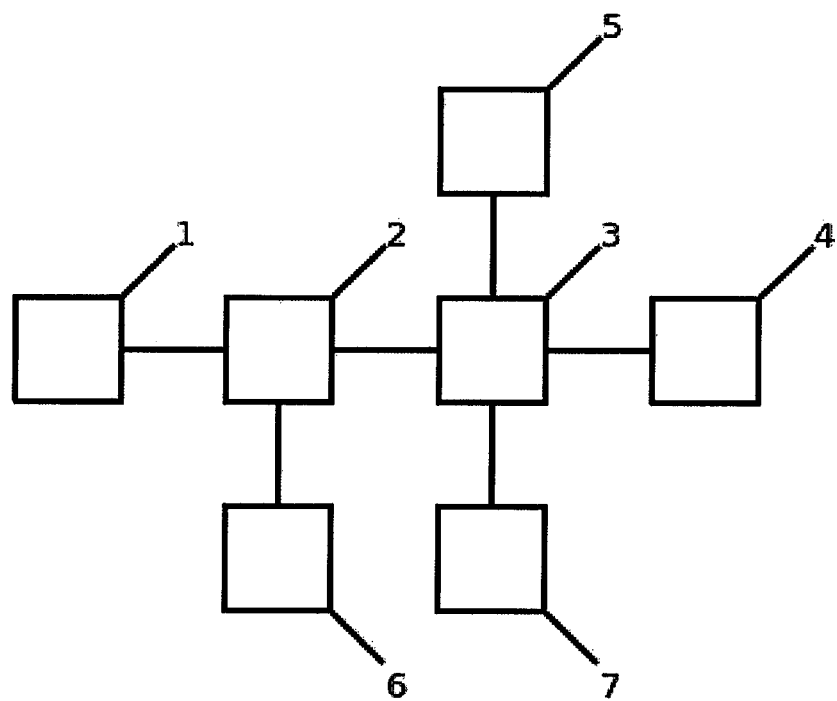
FIG. 14 shows a schematical illustration of a device according to an embodiment which may implement the embodiments of the method according to the invention as described herein.

An embodiment of a device for determining a status of hydration and/or nutrition of tissues in a human body, which is configured to perform the steps of the above methods according to the above or further embodiments is schematically shown in FIG. 14. The device of this embodiment comprises an electrode connection 1 with up to four current injection electrodes and/or up to four voltage measurement electrodes to be applied at limbs extreme points. Both sticky electrodes and contacts are supported. The device further comprises a measurement unit 2, wherein the measured unit 2 performs measurements of the body impedance ($R_i$, and $R_0=R_e$) as described above independently wherein the Cole model is implemented. The device further includes a visualization and processing device 3, which may be embodied as, e.g., smartphone or other device accessing the measurements made and processes them.

The device of this embodiment may further include a remote storage system 4, for example a cloud backup server where measurements may anonymously be stored and further analyzed. Also, a user interface 5 may be provided as part of the device to effect visualization to present the measurement results in a suitable format to the user. Connectivity to further external devices (e.g., printers, a scale for measuring weight (W) and a metering device for measuring height (H) of a human body) and/or manual input and output characteristics for those data are optionally also realized hereby, such as a display with keyboard (or touchscreen) for communicating with the apparatus and allowing to insert the human body's weight and height.

The device of this embodiment also comprises a device storage 6, wherein the acquisition and processing program to carry out the method of the above embodiments etc. is stored. The measurements are also buffered in device storage 6. The device may further have a visualization device storage, wherein raw and processed measurements are stored.

The following processing of BIS measurement, volume calculation and baseline processing may be performed as an embodiment in connection with the device of FIG. 14, wherein at least some of the processing may be realized as a smartphone-app.

A BIS-measurement according to the Cole model is performed and the results are used to calculate $ICW_p$ (Intra Cellular Water) and $ECW_p$ (Extra Cellular Water) fundamental parameters. The calculation method considers individual segments of the human body. The $ICW_p$ and $ECW_p$ expressed in liters is defined as a function body weight (W) which in turn is expressed in kg, body height (H) expressed in cm, extracellular resistance ($R_e$) and intracellular resistance ($R_i$) expressed in Ohms, as described above. The following variants of calculation methods are defined for the implementation:

(a) Using the classical Moissl et al. (2006) equations only (see equations 7 and 8 above), a rough approximation of the required result can be achieved. $R_e$ and $R_i$ refer to wrist-ankle measurements. As noted in the embodiment described above, the corresponding formula and coefficients are shown in Table 1.

TABLE 1

Coefficients using Moissl et al. (2006) equations (eq. (7) and (8) above):

$$ECW = k_{ECW}\left(\frac{h^2\sqrt{w}}{R_e}\right)^{2/3}$$

$$ICW = k_{ICW}\left(\frac{h^2\sqrt{w}}{R_i}\right)^{2/3}$$

$$k_{ECW} = \frac{a}{BMI} + b$$

$$k_{ICW} = \frac{c}{BMI} + d$$

a = 0.188  b = 0.2883  c = 5.8758  d = 0.4194

(b) Using NHANES DXA data an optimized volume calculation is performed, wherein results are obtained by applying least squares fit to NHANES DXA data over 3010 individuals as also described above. By correcting the body fat according to the DXA data and calculating the reversed 3 compartment model the obtained values for ECW and ICW can be corrected. A regression method is then applied to the BIS measurements ($R_e$ and $R_i$) in order to derive a new volume model predicting the corrected ICW and ECW volumes. This volume equation can replace the original Moissl model. The relations shown in Table 2 must be implemented for ECW and ICW calculation from the measured $R_e$, $R_i$.

TABLE 2

Coefficients using DXA data for optimized ECW/ICW volume calculation:

$$ECW = a_0 + a_1 w + a_2 h + a_3 R_e^{-2/3} + a_4 R_i^{-2/3} + a_5 \frac{h}{w} + a_6 \frac{w}{h} \quad (15)$$

$$ICW = b_0 + b_1 w + b_2 h + b_3 R_e^{-2/3} + b_4 R_i^{-2/3} + b_5 \frac{h}{w} + b_6 \frac{w}{h} \quad (16)$$

| | | | |
|---|---|---|---|
| a0 | −5.229 | b0 | −9.149 |
| a1 | 0.331 | b1 | 0.475 |
| a2 | 0.020 | b2 | 0.071 |
| a3 | 1039 | b3 | −245.6 |
| a4 | −230.9 | b4 | 1852 |
| a5 | −0.405 | b5 | −0.0017 |
| a6 | −41.17 | b6 | −65.52 |

This variant, or model, is explained in more detail with reference to FIG. 12. Therein, as indicated on the left side "NHANES measurements" represents measured data (i.e., impedance data $R_e$ and $R_i$ measured via BIS as well as body weight and body height) of 3010 subjects. The top line in FIG. 12 (i.e., STEPS 1 and 2) represents the classical BCS measurement processing based on the Moissl et al. (2006) volume model (see equations (7) and (8) above) and the corresponding 3C model. Accordingly, in STEP 1, the mass or volume fraction of extracellular water ($ECW_1$) and intracellular water ($ICW_1$) are determined, respectively, and in STEP 2, the hydration ($HYD_1$), the body fat ($BF_1$), the normally hydrated adipose tissue ($NH\_AT_1$), and the normally hydrated lean tissue mass ($NH\_LT_1$) are calculated for all of the 3010 subjects in the manner explained with respect to the above embodiments. As noted above, the body fat resulting from this BCS measurement is incorrect, especially for low and high body mass index (BMI) subjects. Therefore, the normally hydrated lean tissue mass ($NH\_LT_1$), the hydration ($HYD_1$) and the body fat ($BF_1$) and/or normally hydrated adipose tissue ($NH\_AT_1$) calculated for all of the 3010 subjects based on the Moissl et al. (2006) volume model are denoted in FIG. 12 as "uncorrected".

At this point, at STEP 3, the (uncorrected) body fat ($BF_1$) is now corrected according to the accurate DXA measurement of body fat. Considering then equation (11) above, since the hydration ($HYD_1$) may be assumed to be correctly determined (which thus equals hydration ($HYD_2$) in FIG. 12) in the measurement in STEP1 and calculation in STEP 2, it is the normally hydrated lean tissue ($NH\_LT_2$) mass or volume fraction, which has to be adjusted:

$NH\_LT_2 + NH\_AT_2 + HYD_2 = \text{TotalBodyWeight} = NH\_LT_1 + NH\_AT_1 + HYD_1$.

If only body fat in $NH\_AT_1$ is corrected to $NH\_AT_2$, thereby holding $NH\_LT_1$ constant, one would obtain a different total body weight as sum of the 3 compartments, which is invalid.

Figure 12:
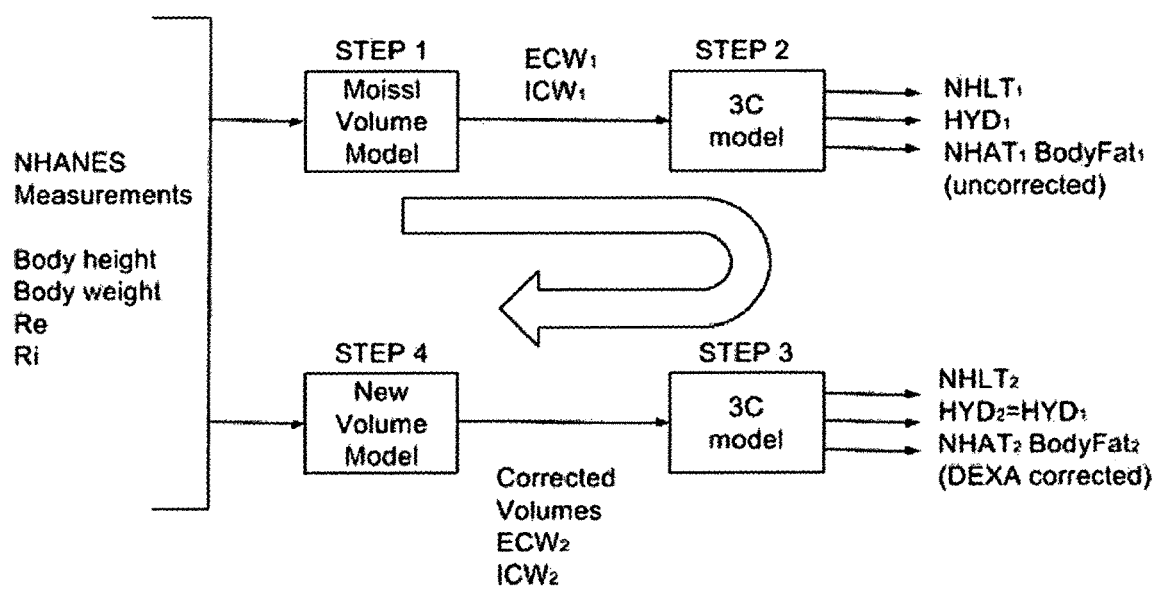
FIG. 12 shows a schematical block diagram illustrating an embodiment of method for setting-up and applying new volume model equations based on body fat which is corrected for prediction errors (e.g., underprediction as compared with accurate DXA measurements) when common volume model equations are applied.

Next, as indicated by the bold arrow in FIG. 12, with the corrected body fat (and also $NH\_AT_2$, $NH\_LT_2$ and $HYD_2$), it is calculated back through the same 3C model in order to get the corrected volumes.

At STEP 4 having the corrected volumes, the above two functions (15) and (16) functions set up which describe extracellular water ($ECW_2$) and intracellular water ($ICW_2$) for the measured BIS data: $ECW(R_e, R_i, h, w)$ and $ICW(R_e, R_i, h, w)$, wherein the coefficients $a_0, \ldots, a_6, b_0, \ldots, b_6$ in Table 2 are determined through regression or fit. More specifically, a set of 3010 impedances $R_e$, $R_i$, and body weights w and body heights h and the set of corresponding 3010 corrected volumes ($ECW_2$ and $ICW_2$) has been obtained through STEPS 3 and 4, and a new function can be built through regression or fit that defines $a_0, \ldots, a_6$, and $b_0, \ldots, b_6$. This function can be used from this point on for any newly measured subject with further BIS-measurements: $R_i$, $R_e$, w, and h. This function, that has been "tailored" on 3010 subjects according to the above method, will calculate correct or at least more accurate values for extracellular water (ECW) and intracellular (ICW) for any other subjects. The 3C model can be used to calculate correctly the compartments and get body fat close to what would be directly measured using DXA.

Once the coefficients of the new volume equations (15) and (16) have been determined through regression or fit of the functions to the data based on DXA measurements, it is not necessary to repeat these steps each time a BIS measurement for another subject is performed using a BIS measurement device. The coefficients $a_0, \ldots, a_6, b_0, \ldots, b_6$ and the functions (15) and (16) are stored in a device 20 as shown in FIG. 1 or 14 and ready to be read out and applied to calculate $ECW_P$ and $ICW_P$.

According to aspects and embodiments of the invention, devices 20 as shown in FIG. 1 or 14 may be implemented with computer hardware and/or software arranged to calculate equations (7) and (8) only, or to calculate equations (15) and (16) only, or with both equations (7) and (8) as well as (15) and (16), e.g., with a selection option for the user which calculation is to be performed in connection with an instant measurement.

It may be noted that coefficients $a_0, \ldots, a_6, b_0, \ldots, b_6$ in Table 2 are not restricted to be determined from NHANES DXA data, and more specifically from 3010 subjects. Data from other surveys using other measurement techniques to determine body fat and/or employing other total numbers of subjects may be employed as well as a basis for the regression or fit.

According to more refined embodiments of the invention, each of the above coefficients $a_0, \ldots, a_6, b_0, \ldots, b_6$ may deviate from the specific values in Table 2 by +/−100%, preferably by +/−50%, and more preferably by +/−20%, and most preferably by +/−10%. However, the scope of the invention is limited by the specific values and ranges.

Also, using equations (7) and (8) methods only (i.e., variant (a)), are encompassed by aspects of the invention wherein body fat is simply corrected by adding an overall percentage to what has been obtained from the measurement results and calculations, or adding a specific percentage only in cases of high and low body fat, where inaccurateness turned out be most prominent.

(c) The above variants (a) and (b) describe how volumes are determined for the full body. In case of measurements involving smaller individual segments such as hand, leg, trunk, or other even smaller segments the following volume calculation method may be applied. It is expected that the total body impedance reflects the sum of individually measured impedances ($Z_i$,) of respective segments. In other words, $$Z_{body} = Z_{arm} Z_{trunk} Z_{leg} \tag{17}$$

Therefore it seems reasonable to calculate individual segment ECW(seg) and ICW(seg) volumes through:

$$ECW_{(seg)} = \alpha_E k_{E(seg)} \frac{h^2}{R_{e(seg)}} \tag{18}$$

$$ICW_{(seg)} = \alpha_I k_{I(seg)} \frac{h^2}{R_{i(seg)}}$$

The volume normalization coefficients are obtained via:

$$\alpha_E = \frac{ECW}{\sum_{seg=1}^{3} k_{E(seg)} \frac{h^2}{R_{e(seg)}}} \tag{19}$$

$$\alpha_I = \frac{ICW}{\sum_{seg=1}^{3} k_{I(seg)} \frac{h^2}{R_{i(seg)}}}$$

ECW and ICW represent the total body volume measurement and the coefficients are then obtained by fitting the NHANES DXA data. Table 3 provides results for these coefficients.

TABLE 3

Coefficients obtained (fit) and/or used for segmental calculation:

| | | | |
|---|---|---|---|
| $k_{E(arm)}$ | 0.531 | $k_{I(arm)}$ | 0.134 |
| $k_{E(trunk)}$ | 0.0514 | $k_{I(trunk)}$ | 0.0124 |
| $k_{E(leg)}$ | 0.450 | $k_{I(leg)}$ | 0.200 |

Above options (a) and (b) may also be combined with option (c).

In the following, an embodiment of the baseline processing algorithm as noted above for use with the device and program is described. This embodiment may be combined with each of above variants (a), (b) and/or (c). Herein, it is expected that the user performs BIS measurements at random times. Therefore a baseline processing function must be applied on a background of a non-uniform sampling. It is assumed that N measurements yield values for ICW(1 ... N), ECW(1 ... N), W(1 ... N), t(1 ... N), the latter representing measurement timestamps expressed in days as floating point numbers.

Given time t as an averaging time (typically 60 days) and a sequence of measurements, more static or baseline values for $ICW_b$, $ECW_b$ and $W_b$ are calculated at times t(1 ... N) through the following steps:

(i) For every timestamp t the time interval [t-τ, t] is considered. If a measurement at t-τ is not available, the previous or next measurement is considered as representative for that time.

(ii) The values of intracellular water (ICW), extracellular water (ECW) and weight (W) are averaged within the interval [t-τ, t] according to:

$$ICW_B(n) = \frac{1}{\tau} \sum_i ICW(i)[t(i+1) - t(i)] \tag{20}$$

$$ECW_B(n) = \frac{1}{\tau} \sum_i ECW(i)[t(i+1) - t(i)]$$

$$w_B(n) = \frac{1}{\tau} \sum_i w(i)[t(i+1) - t(i)]$$

Where count number n is defined for all timestamps from 1 to N, i defines the integration on samples that are within the interval [t-τ,t]. The averaging assumes that a value is held until the next sample.

The dynamic part of the functions is obtained by subtracting the calculated baseline function from the actually determined values of ICW and ECW of each measurement. Also individual segment volumes ECW(seg) and ICW(seg) may be processed according to baseline algorithm.

Namely, for each segment, the segment weight, the segment ICW and the segment ECW can be separated into baseline and dynamic components.

Next, the hydration index may be calculated according to this embodiment. The hydration index HYD (normalized to body weight) is calculated from baseline full body values for ICW and ECW according above noted linear equation, wherein the coefficients are given in Table 4.

Table 4: Coefficients obtained and used for calculation hydration index.

$$HYD_p = a_0 + a_1 ICW_p + a_2 ECW_p$$

where $$ICW_p = ICW_B \frac{100}{w}$$

$$ECW_p = ECW_B \frac{100}{w}$$

$$a_0 = -12.777$$

$$a_1 = -0.429$$

$$a_2 = 1.181$$

According to further embodiments, values for coefficient $a_0$ lie in arrange [−20.0;−3.0], more preferably [−15.0;−7.0], and even more preferably [−13.0;−12.0], and/or values for coefficient $a_1$ lie in arrange [−0.5;−0.3], more preferably [−0.45;−0.4], and even more preferably [−0.435;−0.425], and/or values for coefficient az lie in arrange [0.5;2.0], more preferably [0.8;1.5], and even more preferably [1.1;1.25].

The hydration index may also be calculated with respect to the case where individual segments of the body are considered. The only difference with respect to the full body determination is that the values of ICW and ECW (in units of %) must be calculated with respect to segment weight and not body weight. The segment weights, e.g., $W_{arm}$, $W_{leg}$, or $W_{trunk}$, is obtained by regression of the DXA NHANES data described above and equations along with corresponding coefficients are listed in Table 5. Therein, it may be noted that the trunk weight includes also the weight of the head.

TABLE 5

Segment weight determination and coefficients therefore
$w_{arm} = k_{aw0} + k_{aw1}w + k_{aw2}h$
$w_{leg} = k_{lw0} + k_{lw1}w + k_{lw2}h$
$w_{trunk} = w - 2w_{arm} - 2w_{leg}$

| | | | |
|---|---|---|---|
| $k_{aw0}$ | −1.759 | $k_{lw0}$ | −0.565 |
| $k_{aw1}$ | 0.0596 | $k_{lw1}$ | 0.1649 |
| $k_{aw2}$ | 0.0108 | $k_{lw2}$ | 0.00807 |

Next, the body fat mass (BF), the normally hydrated adipose tissue mass (NH_AT), and the normally hydrated lean tissue mass (NH_LT) as well as muscle mass (MM) may be calculated as in the embodiment explained above.

The segment volume can be also calculated from length (L) and circumferences (C1,C2) according to: Xitron Hydra ECF/ICF (Model 4200) Bioimpedance spectrum analyzer, Issue 1.01 6/97 (1997), Operating Manual Revision 1.02 Xitron Technologies Inc.: San Diego, USA. It may be noted that with a uniform conductor there is only one circumference needed, but if, for example, the leg is viewed as a cone, two circumferences (C1, C2) are needed. References to C1 and C2 and segmental equation is made on page 107 in the Operating Manual.

The steps performed according an embodiment based on the variant (b) corrected for body fat and the baseline algorithm may be summarized as follows:

A. Set-up of new volume equations:
1) BIS Measurement (on, e.g., sample of accurate fat mass DXA measured subjects)
2) Modeling (e.g., Cole model)
3) Determination of $ECW_1$ and $ICW_1$ volume (Moissl et al. (2006) equations (7) and (8), STEP1)
4) Compute 3C model ($NH\_LT_1$, $HYD_1$, and NH_AT (fat mass), see FIG. 12, STEP2)
5a) Replacement of predicted body fat mass (FM) with correct DXA-measured FM for each of the subjects
5b) Calculation of corrected $NH\_LT_2$ based on corrected fat mass for each of the subjects
5c) Determination of corrected ECW and ICW volumes (compare STEP3)
5d) Define new volume equations (15) and (16) for $ECW_2$ and $ICW_2$ with coefficients (compare STEP4)
5e) Regression or fit of function to DXA data for all subjects to determine coefficients in equations
5d) Store new volume equations (15) and (16) and obtained coefficients accounting for corrected body fat B. Apply new volume equations:
6) BIS measurement of another subject, repeat measurements after timesteps (t)
7a) Apply each new volume equations (15) and (16) to obtain ECW(t) and ICW(t)
7b) Time averaging, filtering, and separating ECW and ICW into baseline and dynamic
7c) Define $ECW_B$, $ICW_B$ fraction plane from baseline values
8) Determine Hydration (HYD) from baseline plane
9) Body fat prediction (Xitron)
10) Adipose tissue (NH_AT) determination (fat/0.75)
11) Lean tissue (NH_LT) determination (Weight−NH_AT−HYD)
12) Muscle fraction of NH_LT (e.g., 53% for male, 43% for female)

Steps 1 to 5d may relate to preparatory steps of a device and method for determining the hydration, fitness and/or nutrition status of a human body, or of segments of the human body, while steps 6 to 12 may relate to the device and method itself.

Example Embodiments

Embodiment 1: A method for determining the hydration, fitness and/or nutrition status of a human body, or of segments of the human body, comprising: providing values each of a mass or volume fraction of intracellular water ($ICW_P$) and a mass or volume fraction of extracellular water $ECW_P$) of the human body or the segment; defining a two-dimensional parameter space with a mass or volume fraction of intracellular water (ICW) and a mass or volume fraction of extracellular water (ECW) as separate parameters; determining a reference line within the parameter space, which represents associated values for each of a mass or volume fraction of intracellular water (ICW) and a mass or volume fraction of extracellular water (ECW) of a number of healthy subjects; locating a position within the parameter space which corresponds to the associated values of the mass or volume fraction of intracellular water ($ICW_P$) and the mass or volume fraction of extracellular water ($ECW_P$) of the human body or the segment; determining a distance between the position and the reference line; and deriving a mass or volume, or a mass or volume fraction, of hydration (HYD) from the determined distance for the human body or the segment.

Embodiment 2 The method according to embodiment 1, wherein: the step of providing values includes performing a bioelectric impedance spectroscopy measurement with regard to the human body, wherein an impedance is measured at multiple frequencies applied to the human body or the segment.

Embodiment 3: The method according to embodiment 2, wherein: an extracellular resistance ($R_0$) and an intracellular resistance ($R_I$) are derived from the measured results of the complex impedance at the multiple frequencies, respectively, by computing a model, wherein the model preferably is a Cole-Cole model.

Embodiment 4: The method according to embodiment 3, further comprising: obtaining or measuring a total body weight (W) of the human body or calculating the segment weight; obtaining or measuring a height (H) of the human body or the segment length (L) and/or circumferences (C1, C2); wherein the total body weight (W), the height (H) and/or length (L) and/or circumference (C1, C2), the extracellular resistance ($R_0$) and the intracellular resistance ($R_I$) are used to derive and provide both the mass or volume fraction of intracellular water (ICW) and the mass or volume fraction of extracellular water (ECW) of the human body or the segment.

Embodiment 5: The method according to embodiment 4, wherein: the mass or volume fraction of extracellular water ($ECW_P$) of the human body or the segment is calculated by solving an equation:

$$ECW_{BCS} = k_{ECW}\left(\frac{H^2 \cdot \sqrt{W}}{R_0}\right)^{2/3} \text{ with } k_{ECW} = \frac{a}{BMI} + b$$

wherein BMI is the body mass index of the human body and coefficients a and b are determined by a regression fit of BMI to experimental data of $k_{ECW}$.

Embodiment 6: The method according to embodiments 4 or 5, wherein: the mass or volume fraction of intracellular water ($ICW_P$) of the human body or the segment is calculated by solving an equation:

$$ICW_{BCS} = k_{ICW}\left(\frac{H^2 \cdot \sqrt{W}}{R_1}\right)^{2/3} \text{ with } k_{ICW} = \frac{c}{BMI} + d$$

wherein BMI is the body mass index of the human body and coefficients c and d are determined by a regression fit of BMI to experimental data of $k_{ICW}$.

Embodiment 7: The method according to embodiment 4, wherein: the mass or volume fraction of extracellular water ($ECW_P$) of the human body or the segment is calculated by solving an equation:

$$ECW_{DXA\text{-}opt} = a_0 + a_1 \cdot W + a_2 \cdot H + a_3 \cdot R_e^{-2/3} + a_4 \cdot R_i^{-2/3} + a_5 \cdot H/W + a_6 \cdot W/H,$$

wherein coefficients $a_0, a_1, a_2, a_3, a_4, a_5, a_6$ are obtained by a fit to experimental data.

Embodiment 8: The method according to embodiments 4 or 5, wherein: the mass or volume fraction of intracellular water ($ICW_P$) of the human body or the segment is calculated by solving an equation:

$$ECW_{DXA\text{-}opt} = b_0 + b_1 \cdot W + b_2 \cdot H + b_3 \cdot Re^{-2/3} + b_4 \cdot Ri^{-2/3} + b_5 \cdot H/W + b_6 \cdot W/H,$$

wherein coefficients $b_0, b_1, b_2, b_3, b_4, b_5, b_6$ are obtained by a fit to experimental data.

Embodiment 9: The method according to any of embodiments 1 to 8, wherein: the step of determining the reference line includes providing previously determined experimental data of both the mass or volume fraction of intracellular water (ICW) and the mass or volume fraction of extracellular water (ECW) of a number of healthy subjects, and calculating the reference line by means of linear or non-linear regression.

Embodiment 10: The method according to embodiment 9, wherein positions in the parameter space occupied with same levels of the hydration index define lines parallel to the reference line.

Embodiment 11: The method according to any of embodiments 1 to 10, wherein: the step of deriving a mass or volume, or a mass or volume fraction, of hydration from the determined distance includes calculating a hydration index (HYD) defined as a linear function of the mass or volume fraction of intracellular water (ICW) and the mass or volume fraction of extracellular water (ECW):

$$HYD(ICW_P, ECW_P) = f \cdot ICW_P + g \cdot ECW_P + h;$$

wherein linear coefficients f, g, and h are determined from a fit to experimental data, wherein the hydration index (HYD) represents the mass or volume fraction of hydration, wherein the hydration index is optionally expressed as percentage of total extracellular water (ECW).

Embodiment 12: The method according to embodiment 11, wherein: the determination of the coefficients includes providing previously determined experimental data of the mass or volume fraction of intracellular water (ICW), the mass or volume fraction of extracellular water (ECW) of a number of both healthy and diseased subjects, respectively.

Embodiment 13: The method according to one of embodiments 1 to 12, further comprising: calculating a body fat mass (BF) by subtracting the mass of intracellular water (ICW) and associated materials and the mass of extracellular water (ECW) and associated materials from the total body weight (W) using an equation:

$$BF = 100 - (d_{ECW} \cdot ECW + d_{ICW} \cdot ICW),$$

wherein $d_{ECW}$ and $d_{ICW}$ are the densities of respective extracellular and intracellular fluids and associated materials, and ECW and ICW are respective volume fractions in units of [%].

Embodiment 14: The method according to embodiment 13, further comprising: calculating a mass or volume fraction of a normally hydrated lean tissue mass (NH_LT) defined by subtracting the mass or volume fraction of a normally hydrated adipose tissue mass (NH_AT), which is derived from the body fat mass by dividing the body fat mass with a factor $\vartheta$ accounting for water and associated materials in adipose tissue, and the hydration index (HYD) from the total body weight (W):

$$NH\_LT = 100 - BF/\vartheta - HYD \text{ in units of [\%]},$$

wherein $\vartheta$ is selected between 0.70 and 0.90, preferably between 0.73 and 0.77, and most preferable at or around 0.75.

Embodiment 15: The method according to embodiment 14, further comprising: calculating a muscle mass (MM) as a fraction of the normally hydrated lean tissue mass (NH_LT).

Embodiment 16: The method according to embodiment 15, wherein: the fraction of muscle mass (MM) is selected to be between 30% and 60% of the normally hydrated lean tissue mass (NH_LT), and more preferably between 40% and 60%.

Embodiment 17: The method according to embodiment 3, wherein the step of providing values each of a mass or volume fraction of intracellular water ($ICW_P$) and a mass or volume fraction of extracellular water ($ECW_P$) is performed for each of two or more segments (leg, trunk, arm) of the human body, separately, wherein the total body impedance is the sum of individually measured impedances ($Z_i$) of respective segments; wherein the mass or volume fraction of intracellular water ($ICW_P$) and the mass or volume fraction of extracellular water ($ECW_P$) are preferably calculated for each individual segment through:

$$ECW_{(seg)} = \alpha_E k_{E(seg)} \frac{h^2}{R_{e(seg)}}$$

$$ICW_{(seg)} = \alpha_I k_{I(seg)} \frac{h^2}{R_{i(seg)}}$$

wherein the volume normalization coefficients $\alpha_E$ and $\alpha_I$ are obtained via:

$$\alpha_E = \frac{ECW}{\sum_{seg=1}^{3} k_{E(seg)} \frac{h^2}{R_{e(seg)}}}$$

$$\alpha_I = \frac{ICW}{\sum_{seg=1}^{3} k_{I(seg)} \frac{h^2}{R_{i(seg)}}}$$

and the coefficients $k_E$ and $k_I$ are obtained through a fit to empirical data.

Embodiment 18: The method according to any of embodiments 1 through 17, wherein the step of providing values each of a mass or volume fraction of intracellular water ($ICW_P$) and a mass or volume fraction of extracellular water (ECW$_P$) of the human body are repeated a number (N) of times, wherein, by means of averaging, or filtering, or a Fourier transformation with regard to time, the mass or volume fraction of intracellular water (ICW) and the mass or volume fraction of extracellular water (ECW) and the weight (W) are separated into: (i) a static or nearly static baseline component of mass or volume fraction of intracellular water (ICW$_B$) and mass or volume fraction of extracellular water (ECW$_B$) and weight (W$_B$), and (ii) a dynamically changing component of mass or volume fraction of intracellular water (ICW$_D$) and mass or volume fraction of extracellular water (ECW$_D$) and weight (W$_D$), wherein:

ICW=ICW$_B$+ICW$_d$

ECW=ECW$_B$+ECW$_d$ $w=w_B+w_d$

Embodiment 19: The method according to embodiment 18, further comprising: performing the steps of (i) defining a two-dimensional parameter space, (ii) determining a reference line within the parameter space, (iii) locating a position within the parameter space, (iv) determining a distance between the position and the reference line, and (v) deriving a mass or volume, or a mass or volume fraction (HYD) of hydration from the determined distance based on the static or nearly static baseline component of mass or volume fraction of intracellular water (ICW$_B$) and mass or volume fraction of extracellular water (ECW$_B$) and weight (W$_B$) only; determining a body fat mass (BF) from static or nearly static baseline component of mass or volume fraction of intracellular water (ICW$_B$) and mass or volume fraction of extracellular water (ECW$_B$) and weight (W$_B$); determining a normally hydrated adipose tissue mass (NH_AT) from the body fat mass (BF); determining a normally hydrated lean tissue mass (NH_LT) from the mass or volume fraction of hydration (HYD) and the normally hydrated adipose tissue mass (NH_AT); wherein: (a) the dynamically changing component of mass or volume fraction of intracellular water (ICW$_D$), (b) the dynamically changing component of mass or volume fraction of extracellular water (ECW$_D$), (c) the hydration index (HYD), (d) the normally hydrated lean tissue mass (NH_LT), and (e) the normally hydrated adipose tissue mass (NH_AT) form a 5 compartment (5C) model.

Embodiment 20: A method for determining the hydration, fitness and/or nutrition status of a human body, comprising: providing values each of a mass or volume fraction of intracellular water (ICW$_P$) and a mass or volume fraction of extracellular water (ECW$_P$) of the human body; deriving a mass or volume, or a mass or volume fraction, of a hydration by calculating a hydration index (HYD) defined as a linear function of the mass or volume fraction of intracellular water (ICW) and the mass or volume fraction of extracellular water (ECW), which is given by HYD (ICW$_P$, ECW$_P$)=$f$·ICW$_P$+$g$·ECW$_P$+$h$;

wherein linear coefficients f, g, and h are determined from a fit to previously obtained experimental data of both healthy subjects and human bodies suffering from over and/or under hydration, wherein the hydration index (HYD) represents the mass or volume fraction associated with hydration.

Embodiment 21: The method according to embodiment 20, wherein: the step of providing values includes performing a bioelectric impedance spectroscopy measurement with regard to the human body, wherein an impedance is measured at multiple frequencies applied to the human body.

Embodiment 22: The method according to embodiment 21, wherein: an extracellular resistance (R$_0$) and an intracellular resistance (R$_I$) are derived from the measured results of the impedance at the multiple frequencies, respectively.

Embodiment 23: The method according to embodiment 22, further comprising: obtaining or measuring a total body weight (W) of the human body; obtaining or measuring a size (H) of the human body; wherein the total body weight (W), the size (H), the extracellular resistance (R$_0$) and the intracellular resistance (R$_I$) are used to derive and provide both the mass or volume fraction of intracellular water (ICW) and the mass or volume fraction of extracellular water (ECW) of the human body.

Embodiment 24: The method according to embodiment 23, wherein: the mass or volume fraction of extracellular water (ECW) of the human body is calculated by solving an equation:

$$ECW_{BCS} = k_{ECW}\left(\frac{H^2 \cdot \sqrt{W}}{R_0}\right)^{2/3} \text{ with } k_{ECW} = \frac{a}{BMI} + b$$

wherein BMI is the body mass index of the human body and coefficients a and b are determined by a regression fit of BMI to previously obtained experimental data of $k_{ECW}$.

Embodiment 25: The method according to embodiments 23 or 24, wherein: the mass or volume fraction of intracellular water (ICW) of the human body is calculated by solving an equation:

$$ICW_{BCS} = k_{ICW}\left(\frac{H^2 \cdot \sqrt{W}}{R_I}\right)^{2/3} \text{ with } k_{ICW} = \frac{c}{BMI} + d$$

wherein BMI is the body mass index of the human body and coefficients c and d are determined by a regression fit of BMI to previously experimental data of $k_{ICW}$.

Embodiment 26: A method for setting up a set of volume model equations for use in determining the hydration, fitness and/or nutrition status of a human body, or of segments of the human body, comprising: defining a sample of multiple subjects, and for each of the subjects: calculating (STEP1) a mass or volume fraction of extracellular water (ECW$_1$) and of intracellular water (ICW$_1$), respectively, using a set of first volume model equations, calculating (STEP2) each a first value of a mass or volume fraction of hydration (HYD$_1$, HYD$_2$), a predicted body fat mass or volume fraction (BF$_1$), and a normally hydrated lean tissue mass or volume fraction (NH_LT$_1$) of a 3C compartment model, based on the mass or volume fraction of intracellular water (ICW$_1$) and the mass or volume fraction of extracellular water (ECW$_1$), determining each a second value of a body fat mass or volume fraction (BF$_2$) from experimental results, replacing the first value of the predicted body fat mass or volume fraction (BF) with the second value of body fat mass or volume fraction (BF$_2$) to correct for an prediction errors of body fat, adjusting (STEP3) the normally hydrated lean tissue mass or volume fraction (NH_LT$_2$) in response to the corrected body fat mass (BF$_2$), adjusting (STEP 4) the mass or volume fraction of extracellular water (ECW$_2$) and of intracellular water (ICW$_2$), respectively; and setting up a set of second volume model equations each for determining the mass or volume fraction of extracellular water (ECW$_2$) and of intracellular water (ICW$_2$), respectively, determining coefficients in the second volume model equations by a regression or fit of the second volume model equations to experimental data for each of the subjects with respect to measured values each of a mass or volume fraction of extracellular water (ECW) and of intracellular water (ICW).

Embodiment 27: The method according to embodiment 26, further comprising obtaining an extracellular resistance ($R_0$), an intracellular resistance ($R_I$), a weight (w) and a height (h) for each of the subjects of the sample, which are measured via bio-impedance spectroscopy, and determining each the mass or volume fraction of extracellular water ($ECW_1$) and the mass or volume fraction of intracellular water ($ICW_1$) from the extracellular resistance ($R_0$) and an intracellular resistance ($R_I$), the weight (w) and the height (h) using the set of first volume model equations.

Embodiment 28: The method according to embodiment 26, wherein the set of first model equations is:

$$ECW_{BCS} = k_{ECW} \left( \frac{H^2 \cdot \sqrt{W}}{R_0} \right)^{2/3} \text{ with } k_{ECW} = \frac{a}{BMI} + b \text{ and}$$

$$ICW_{BCS} = k_{ICW} \left( \frac{H^2 \cdot \sqrt{W}}{R_I} \right)^{2/3} \text{ with } k_{ICW} = \frac{c}{BMI} + d$$

wherein BMI is the body mass index of the human body, coefficients a and b are determined by a regression fit of BMI to experimental data of $k_{ECW}$, and coefficients c and d are determined by a regression fit of BMI to experimental data of $k_{ICW}$.

Embodiment 29: The method of embodiment 26, wherein: the set of second volume equations is:

$$ECW_{DXA-opt} = a_0 + a_1 \cdot W + a_2 \cdot H + a_3 \cdot R_e^{-2/3} + a_4 \cdot R_i^{-2/3} + a_5 \cdot H/W + a_6 \cdot W/H, \text{ and}$$

$$ICW_{DXA-opt} = b_0 + b_1 \cdot W + b_2 \cdot H + b_3 \cdot Re^{-2/3} + b_4 \cdot Ri^{-2/3} + b_5 \cdot H/W + b_6 \cdot W/H,$$

wherein the coefficients $a_0, a_1, a_2, a_3, a_4, a_5, a_6$ are obtained by a first fit to the experimental data, and the coefficients $b_0, b_1, b_2, b_3, b_4, b_5, b_6$ are obtained by a second fit to the experimental data.

Embodiment 30: A method for determining the hydration, fitness and/or nutrition status of a human body, or of segments of the human body, comprising: providing values each of mass or volume, or a mass or volume fraction of intracellular water ($ICW_P$) and a mass or volume, or mass or volume fraction of extracellular water ($ECW_P$) of the human body or the segment; deriving a mass or volume, or a mass or volume fraction, of hydration (HYD) from the provided values; calculating a body fat mass (BF) by subtracting the mass or volume, or a mass or volume fraction of intracellular water (ICW) and associated materials and the mass or volume, or a mass or volume fraction of extracellular water (ECW) and associated materials from the total body weight (W), respectively, calculating a mass or volume fraction of a normally hydrated adipose tissue (NH_AT) by dividing the body fat mass with a factor ϑ accounting for water and associated materials in adipose tissue, wherein ϑ is selected between 0.70 and 0.90, preferably between 0.73 and 0.77, and most preferable at or around 0.75, and calculating a mass or volume fraction of a normally hydrated lean tissue mass (NH_LT) by subtracting the mass or volume fraction of a normally hydrated adipose tissue (NH_AT) and mass or volume fraction, of hydration (HYD) from total body weight, respectively.

Embodiment 31: A method for determining the hydration, fitness and/or nutrition status of a human body, or of segments of the human body, comprising: providing values each of a mass or volume fraction of intracellular water ($ICW_P$) and a mass or volume fraction of extracellular water ($ECW_P$) of the human body or the segment; wherein the step of providing values each of a mass or volume fraction of intracellular water ($ICW_P$) and a mass or volume fraction of extracellular water ($ECW_P$) of the human body are repeated a number (N) of times, wherein, by means of averaging, or filtering, or a Fourier transformation with regard to time, the mass or volume fraction of intracellular water (ICW) and the mass or volume fraction of extracellular water (ECW) and the weight (W) are separated into: (i) a static or nearly static baseline component of mass or volume fraction of intracellular water ($ICW_B$) and mass or volume fraction of extracellular water ($ECW_B$) and weight ($W_B$), and (ii) a dynamically changing component of mass or volume fraction of intracellular water ($ICW_D$) and mass or volume fraction of extracellular water ($ECW_D$) and weight ($W_D$), wherein:

$$ICW = ICW_B + ICW_d$$

$$ECW = ECW_B + ECW_d$$

$$w = w_B + w_d$$

Embodiment 32: The method according to embodiment 31, wherein: the steps of repeatedly providing values includes performing a bioelectric impedance spectroscopy measurement with regard to the human body, wherein an impedance is measured at multiple frequencies applied to the human body or the segment.

Embodiment 33: The method according to embodiment 32, wherein: an extracellular resistance ($R_0$) and an intracellular resistance ($R_I$) are derived from the measured results of the complex impedance at the multiple frequencies, respectively, by computing a model, wherein the model preferably is a Cole-Cole model.

Embodiment 34: The method according to embodiment 33, further comprising: obtaining or measuring a total body weight (W) of the human body or calculating the segment weight; obtaining or measuring a height (H) of the human body or the segment length (L) and/or circumferences (C1, C2); wherein the total body weight (W), the height (H) and/or length (L) and/or circumference (C1, C2), the extracellular resistance ($R_0$) and the intracellular resistance ($R_I$) are used to derive and provide both the mass or volume fraction of intracellular water (ICW) and the mass or volume fraction of extracellular water (ECW) of the human body or the segment at each time step.

Embodiment 35: The method according to embodiment 34, wherein: the mass or volume fraction of extracellular water ($ECW_P$) of the human body or the segment is calculated by solving an equation:

$$ECW_{BCS} = k_{ECW} \left( \frac{H^2 \cdot \sqrt{W}}{R_0} \right)^{2/3} \text{ with } k_{ECW} = \frac{a}{BMI} + b$$

wherein BMI is the body mass index of the human body and coefficients a and b are determined by a regression fit of BMI to experimental data of $k_{ECW}$.

Embodiment 36: The method according to embodiments 34 or 35, wherein: the mass or volume fraction of intracellular water ($ICW_P$) of the human body or the segment is calculated by solving an equation:

$$ICW_{BCS} = k_{ICW}\left(\frac{H^2 \cdot \sqrt{W}}{R_I}\right)^{2/3} \text{ with } k_{ICW} = \frac{c}{BMI} + d$$

wherein BMI is the body mass index of the human body and coefficients c and d are determined by a regression fit of BMI to experimental data of $k_{ICW}$.

Embodiment 37: The method according to embodiment 34, wherein: the mass or volume fraction of extracellular water ($ECW_P$) of the human body or the segment is calculated by solving an equation:

$$ECW_{DXA\text{-}opt} = a_0 + a_1 \cdot W + a_2 \cdot H + a_3 \cdot R_e^{-2/3} + a_4 \cdot R_i^{-2/3} + a_5 \cdot H/W + a_6 \cdot W/H,$$

wherein coefficients $a_0, a_1, a_2, a_3, a_4, a_5, a_6$ are obtained by a fit to experimental data.

Embodiment 38: The method according to embodiments 34 or 35, wherein: the mass or volume fraction of intracellular water ($ICW_P$) of the human body or the segment is calculated by solving an equation:

$$ICW_{DXA\text{-}opt} = b_0 + b_1 \cdot W + b_2 \cdot H + b_3 \cdot Re^{-2/3} + b_4 \cdot Ri^{-2/3} + b_5 \cdot H/W + b_6 \cdot W/H,$$

wherein coefficients $b_0, b_1, b_2, b_3, b_4, b_5, b_6$ are obtained by a fit to experimental data.

Embodiment 39: The method according to embodiment 31, further comprising: performing a step of deriving a mass or volume, or a mass or volume fraction of hydration (HYD) based on the static or nearly static baseline component of mass or volume fraction of intracellular water ($ICW_B$) and mass or volume fraction of extracellular water ($ECW_B$) and weight ($W_B$) only; determining a body fat mass (BF) and/or a normally hydrated adipose tissue mass (NH_AT) from static or nearly static baseline component of mass or volume fraction of intracellular water ($ICW_B$) and mass or volume fraction of extracellular water ($ECW_B$) and weight ($W_B$) only; and determining a normally hydrated lean tissue mass (NH_LT) from the mass or volume fraction of hydration (HYD) and the normally hydrated adipose tissue mass (NH_AT); wherein: (a) the dynamically changing component of mass or volume fraction of intracellular water ($ICW_D$), (b) the dynamically changing component of mass or volume fraction of extracellular water ($ECW_D$), (c) the hydration index (HYD), (d) the normally hydrated lean tissue mass (NH_LT), and (e) the normally hydrated adipose tissue mass (NH_AT) form a 5 compartment (5C) model.

Embodiment 40: A device for determining the hydration, fitness and/or nutrition status of a human body, comprising: an input and/or measurement unit for performing a step of providing values each of a mass or volume fraction of intracellular water (ICW) and a mass or volume fraction of extracellular water (ECW) of the human body; a processor unit for performing steps of (a) defining a two-dimensional parameter space with a mass or volume fraction of intracellular water (ICW) and a mass or volume fraction of extracellular water (ECW) as separate parameters; (b) determining a reference line within the parameter space, which represents associated values for each of a mass or volume fraction of intracellular water (ICW) and a mass or volume fraction of extracellular water (ECW) of a number of healthy subjects; (c) locating a position within the parameter space which corresponds to the associated values of the mass or volume fraction of intracellular water (ICW) and the mass or volume fraction of extracellular water (ECW) of the human body; (d) determining a distance between the position and the reference line; (e) deriving and outputting a mass or volume, or a mass or volume fraction, of hydration from the determined distance for the human body.

Embodiment 41: The device for determining a status of hydration and/or nutrition of tissues in a human body, comprising: an input and/or measurement unit for performing a step of providing values each of a mass or volume fraction of intracellular water (ICW) and a mass or volume fraction of extracellular water (ECW) of the human body; a processor unit for performing a step of deriving and outputting a mass or volume, or a mass or volume fraction, of a hydration by calculating a hydration index (HYD) defined as a linear function of the mass or volume fraction of intracellular water (ICW) and the mass or volume fraction of extracellular water (ECW), which is given by $$\text{HYD (ICW, ECW)} = f \cdot ICW + g \cdot ECW + h;$$

wherein linear coefficients f, g, and h are determined from a fit to previously obtained experimental data of both healthy and diseased patients, wherein the hydration index (HYD) is a mass or volume fraction of a hydration.

Embodiment 42: A computer program product, comprising instructions which, when the program is executed by a computer, cause the computer to carry out the steps of the method of embodiments 1 or 20.

Embodiment 43: The computer-readable storage medium comprising instructions which, when executed by a computer, cause the computer to carry out the steps of the method of claim 1 or 20.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A method for determining the hydration, fitness and/or nutrition status of a human body, or of segments of the human body, comprising the steps of:
determining values each of a mass or volume fraction of intracellular water ($ICW_P$) and a mass or volume fraction of extracellular water ($ECW_P$) of the human body or the segment, which includes performing a bioelectric impedance spectroscopy measurement with regard to the human body, wherein an impedance is measured at multiple frequencies applied to the human body or the segment;
defining a two-dimensional parameter space with a mass or volume fraction of intracellular water ($ICW_P$) and a mass or volume fraction of extracellular water ($ECW_P$) as separate parameters;
determining a reference line within the parameter space, which represents associated values for each of a mass or volume fraction of intracellular water ($ICW_P$) and a mass or volume fraction of extracellular water ($ECW_P$) of a number of healthy subjects;
locating a position within the parameter space which corresponds to the associated values of the mass or volume fraction of intracellular water ($ICW_P$) and the mass or volume fraction of extracellular water ($ECW_P$) of the human body or the segment;
determining a distance between the position and the reference line;
deriving a mass or a volume, or a mass fraction or a volume fraction, of hydration (HYD) from the determined distance for the human body or the segment;

determining a body fat mass (BF) from the determined values of mass or volume fractions of intracellular water ($ICW_P$) and the mass or volume fraction of extracellular water ($ECW_P$) of the human body or the segment;

determining a normally hydrated lean tissue mass (NH_LT) from the determined values of hydration (HYD) and body fat mass (BF).

2. The method according to claim 1, wherein:

an extracellular resistance ($R_0$) and an intracellular resistance ($R_I$) are derived from the measured results of the complex impedance at the multiple frequencies, respectively, by computing a model.

3. The method according to claim 2, further comprising:

obtaining or measuring a total body weight (W) of the human body;

obtaining or measuring a height (H) of the human body;

determining the values each of a mass or volume fraction of intracellular water ($ICW_P$) and a mass or volume fraction of extracellular water ($ECW_P$) of the human body as a function of the total body weight (W), the height (H), the extracellular resistance ($R_0$), and the intracellular resistance ($R_I$).

4. The method according to claim 3, wherein:

the mass or volume fraction of extracellular water ($ECW_P$) of the human body or the segment is calculated by solving an equation:

$$ECW_{DXA-opt}=a_0+a_1 \cdot W+a_2 \cdot H+a_3 \cdot R_e^{-2/3}+a_4 \cdot R_i^{-2/3}+a_5 \cdot H/W+a_6 \cdot W/H,$$

wherein coefficients $a_0, a_1, a_2, a_3, a_4, a_5, a_6$ are obtained by a fit to experimental data.

5. The method according to claim 3, wherein:

the mass or volume fraction of intracellular water ($ICW_P$) of the human body or the segment is calculated by solving an equation:

$$ICW_{DXA-opt}=b_0+b_1 \cdot W+b_2 \cdot H+b_3 \cdot Re^{-2/3}+b_4 \cdot Ri^{-2/3}+b_5 \cdot H/W+b_6 \cdot W/H,$$

wherein coefficients $b_0, b_1, b_2, b_3, b_4, b_5, b_6$ are obtained by a fit to experimental data.

6. The method according to claim 1, wherein:

the step of determining the reference line includes providing previously determined experimental data of both the mass or volume fraction of intracellular water (ICW) and the mass or volume fraction of extracellular water (ECW) of a number of healthy subjects, and calculating the reference line by means of linear or non-linear regression.

7. The method according to claim 1, wherein:

the step of deriving a mass or volume, or a mass or volume fraction, of hydration from the determined distance includes calculating a hydration index (HYD) defined as a linear function of the mass or volume fraction of intracellular water (ICW) and the mass or volume fraction of extracellular water (ECW), wherein the hydration index (HYD) represents the mass or volume fraction of hydration, and wherein the hydration index is optionally expressed as a percentage of total extracellular water (ECW), wherein the linear function is optionally expressed as:

$$HYD(ICW_P, ECW_P)=f \cdot ICW_P+g \cdot ECW_P+h;$$

wherein linear coefficients f, g, and h are determined from a fit to experimental data.

8. The method according to claim 1, wherein:

determining a body fat mass (BF) includes subtracting the mass of intracellular water (ICW) and associated materials and the mass of extracellular water (ECW) and associated materials from the total body weight (W) using an equation:

$$BF=100-(d_{ECW} \cdot ECW+d_{ICW} \cdot ICW),$$

wherein $d_{ECW}$ and $d_{ICW}$ are the densities of respective extracellular and intracellular fluids and associated materials, and ECW and ICW are respective volume fractions in units of [%].

9. The method according to claim 1, wherein:

determining a mass or volume fraction of a normally hydrated lean tissue mass (NH_LT) includes subtracting the mass or volume fraction of a normally hydrated adipose tissue mass (NH_AT), which is derived from the body fat mass by dividing the body fat mass with a factor $\vartheta$ accounting for water and associated materials in adipose tissue, and the hydration index (HYD) from the total body weight (W):

$$NH\_LT=100-BF/\vartheta-HYD \text{ in units of } [\%],$$

wherein $\vartheta$ is selected between 0.70 and 0.90.

10. The method according to claim 2, further comprising:

determining the segment weight or segment volume;

obtaining the segment length (L) and/or circumferences (C1, C2); and determining the values each of a mass or volume fraction of intracellular water ($ICW_P$) and a mass or volume fraction of extracellular water ($ECW_P$) of the segment by using the segment weight or segment volume, the length (L) and/or circumference (C1, C2) of the segment, the extracellular resistance ($R_0$), and the intracellular resistance ($R_I$).

11. A device for determining the hydration, fitness and/or nutrition status of a human body, comprising:

an input and/or measurement unit for performing a step of providing a total bodyweight (W) of the human body or a weight or volume of a segment, a height (H) of the human body or a length (L) and/or circumferences (C1, C2) of the segment, and of an extracellular resistance ($R_0$) and an intracellular resistance ($R_I$) obtained via a bioelectric impedance spectroscopy measurement; and a processor unit for performing method steps according to one of claim 1.

12. A computer program product, comprising instructions which, when the program is executed by a computer, cause the computer to carry out the steps of the method of claim 1.

13. A computer-readable storage medium comprising instructions which, when executed by a computer, cause the computer to carry out the steps of the method of claim 1.

* * * * *